United States Patent [19]
Douvas et al.

[11] Patent Number: 5,707,626
[45] Date of Patent: Jan. 13, 1998

[54] METHODS OF TREATING HIV INFECTION USING ANTIBODIES TO THE U2 SMALL NUCLEAR RIBONUCLEAR PROTEIN

[75] Inventors: Angeline Douvas, Claremont; Yoshi Takehana, Long Beach; Glenn Ehresmann, Altadina, all of Calif.

[73] Assignee: University of Southern California, Los Angeles, Calif.

[21] Appl. No.: 704,170

[22] Filed: Aug. 28, 1996

Related U.S. Application Data

[63] Continuation of Ser. No. 29,850, Mar. 11, 1993, abandoned.
[51] Int. Cl.$^6$ ................................................. A61K 39/42
[52] U.S. Cl. ........................... 424/100.1; 424/148.1; 424/152.1; 424/172.1
[58] Field of Search ..................... 424/142.1, 148.1, 424/152.1, 156.1, 160.1, 172.1, 188.1, 208.1; 530/358, 388.15, 388.35, 388.85, 389.1, 389.4

[56] References Cited

U.S. PATENT DOCUMENTS

| | | |
|---|---|---|
| 2,843,889 | 1/1958 | Puri . |
| 5,137,805 | 8/1992 | Kingston et al. ........................ 435/6 |

OTHER PUBLICATIONS

Vittecoq et al., *Proc. Nat'l. Acad. Sci.*, USA 92:1195–1199, Feb., 1995.
Ho, D.D., *Science* 272:1124–1125, 24 May 1996.
Mellors, et al., *Science* 272:1167–1170, 24 May 1996.
Fahey et al., "Status of Immune–based Therapies in HIV Infection and AIDS," *Clin. Exp. Immunol.* 88:1–5, 1992.
Fox, J.L., "No Winners Against AIDS", *Bio/Technology* 12:128, Feb. 1994.
Douvas et al. Cross–reactivity between Autoimmune Anti–U1 snRNP Abs. & Neutralizing Epitopes of HIV–1 gp120/41 Aids. Res. Hum. Retroviruses 10:253 1994.
Passive Immunization The Merck Index pp. 1948–1949 16th edition 1992.
Stein et al. Immune–based Therapeutics: Scientific Rationale and The Promising Approach to the Treatment of HIV Infected Individual Clin. Infect. Dis. 17:749, 1995.
Cronstein et al. The Adhesion Molecules of Inflammation Arthritis & Rheumatism 36:147 1993.
Buckley et al. The Use of Intravenous Immune Globulin in Immunodeficiency Diseases NEJM Jul. 11, 1991 pp. 110–117.
Ngou et al. Ab Responses Against Polypeptide Components of EDU Induced Early Diffuse Ag in Patients with MCTD J. Med Virol. 32:34, 1990.
Stiehm et al. Intravenous Igs as Therapeutic Agents Ann. Internal Med. 107:367, 1987.
Albrecht, M.A., et al., "The Herpes Simplex Virus Immediate—Early Protein, ICP4, Is Required To Potentiate Replication Of Human Immunodeficiency Virus In CD4+ Lymphocytes" *J. Virol.*, vol. 63, No. 5, 1861–1868 (May 1989).
Bandziulis, R.J., et al., "RNA–Binding Proteins As Developmental Regulators" *Genes & Devel.*, 3, 431–437 (1989).
Berget, S.M., et al., "U1, U2, And U4/U6 Small Nuclear Ribonucleoproteins Are Required For In Vitro Splicing But Not Polyadenylation" *Cell*, vol. 46, 691–696 (Aug. 29, 1986).
Bjorkman, P.J., et al., "The Foreign Antigen Binding Site And T Cell Recognition Regions Of Class 1 Histocompatibility Antigens" *Nature*, vol. 329, 512–518 (Oct. 8, 1987).
Black, D.L., et al., "U2 As Well As U1 Small Nuclear Ribonucleoprotein Are Involved In Premessenger RNA Splicing" *Cell*, vol. 42, 737–750 (Oct. 1985).
Boelens, W., et al., "Analysis Of In Vitro Binding Of U1–A Protein Mutants To U1 snRNA" *Nuc. Acid Res.*, vol. 19, No. 17, 4611–4618 (1991).
Bringmann, P., et al., "Purification Of The Individual snRNPs U1, U2, U5 And U4/U6 From HeLa Cells And Characterization Of Their Protein Constituents" *The EMBO Journal*, vol. 5, No. 13, 3509–3516 (1986).
Broliden, P.A., et al., "Identification Of Human Neutralization–Inducing Regions Of The Human Immunodeficiency Virus Type 1 Envelope Glycoproteins" *Proc. Natl. Acad. Sci. USA*, vol. 89, 461–465 (Jan. 1992).
Calin, A., et al., "Genetic Differences Between B27 Positive Patients With Ankylosing Spondylitis And B27 Positive Healty Controls"*Arthritis and Rheumatism*, vol. 26, No. 12, 1460–1464 (Dec. 1983).
Chou, P.Y., et al., "Empirical Predictions Of Protein Conformation" *Ann. Rev. Biochem.*, 47:251–76, 251–276 (1978).
Cram, D.S., et al., "Mapping Of Multiple B Cell Epitopes On The 70–Kilodalton Autoantigen Of The U1 Ribonucleoprotein Complex" *J. Immunol.* vol. 145, No. 2, 630–635 (Jul. 15, 1990).
Crow, M.K., et al., "Human Peripheral Blood T Helper Cell–Induced B Cell Activation Results In B Cell Surface Expression Of The CD23 (BLAST–2) Antigen" *Cell. Immunol.*, 121, 99–112 (1989).
Devereux, J., et al., "A Comprehensive Set Of Sequence Analysis Programs For The VAX" *Nuc. Acid Res.*, vol. 12, No. 1, 387–395 (1984).
Douvas, A., et al., "Multiple Overlapping Homologies Between Two Rheumatoid Antigens And Immunosuppressive Viruses" *Proc. Natl. Acad. Sci. USA*, vol. 88, 6328–6332 (Jul. 1991).

(List continued on next page.)

*Primary Examiner*—Robert D. Budens
*Attorney, Agent, or Firm*—Robbins, Berliner & Carson

[57] ABSTRACT

Therapeutic strategies for the treatment of immunoinfective cluster virus infections in humans involving the use of antibodies or fragments thereof which are characteristic of autoantibodies produced by patients affected with systemic rheumatic disorders and cross-react with epitopes on an immunoinfective cluster virus. Additional therapeutic strategies include the use U1 RNA or fragments thereof to treat said viral infections.

1 Claim, 15 Drawing Sheets

OTHER PUBLICATIONS

Douvas, A.S., et al., "Isolation And Characterization Of Nuclear Ribonucleoprotein Complexes Using Human Anti-Nuclear Ribonucleoprotein Antibodies" *J. Biol. Chem.*, vol. 254, No. 9, 3608–3616 (May 10, 1979).

Douvas, A.S., "Autoantibodies Occuring In Two Different Theumatic Diseases React With The Same Nuclear Ribonucleoprotein Particle" *Proc. Natl. Acad. Sci. USA*, vol. 79, 5401–5405 (Sep. 1982).

Dower, S.K., et al., "Phosphorus–31 Nuclear Magnetic Resonance Probes For The Combining Site Of The Myeloma Protein M315" *Biochem.*, vol. 18, No. 17, 3668–3674 (1979).

Durda, P.J., et al., "HIV–1 Neutralizing Monoclonal Antibodies Induced By A Synthetic Peptide" *AIDS Res. Hum. Retro.*, vol. 6, No. 9, 1115–1123 (1990).

Earnshaw, W.C., et al., "Molecular Cloning Of cDNA For CENP–B, The Major Human Centromere Autoantigen" *J. Cell. Biol.*, 104, 817–829 (1987).

Emini, E.A., et al., "Induction Of Hepatitis A Virus–Neutralizing Antibody By A Virus–Specific Synthetic Peptide" *J. Virol.*, vol. 55, No. 3, 836–839 (Sep. 1985).

Ewing, C., et al., "Antibody Activity In Ankylosing Spondylitis Sera To Two Sites On HLA B27.1 At The MHC Groove Region (Within Sequence 65–85), And To A *Klebsiella Pneumoniae* Nitrogenase Reductase Peptide (Within Sequence 181–199)" *J.Exp. Med.*, vol. 171, 1635–1647 (May 1990).

Fox, R., "Epstein–Barr Virus And Human Autoimmune Diseases: Posibilities And Pitfalls" *J. Virol. Meth.*, 21, 19–27 (1988).

Fox, R., et al., "Potential Role Of Epstein–Barr Virus In Sjögren's Syndrome" *Rheumatic Disease Clinics of North America*, vol. 13, No. 2, 275–292 (Aug. 1987).

Gimble, J.M., et al., "Activation Of The Human Immunodeficiency Virus Long Terminal Repeat By Herpes Simplex Virus Type 1 Is Associated With Induction Of A Nuclear Factor That Binds To The NF–κB/Core Enhancer Sequence" *J. Virol.*, vol. 62, 4104–4112 (Nov. 1988).

Girard, M., et al., "Immunization Of Chimpanzees Confers Protection Against Challenge With Human Immunodeficiency Virus" *Proc. Natl. Acad. Sci. USA*, vol. 88, 542–546 (Jan. 1991).

Glockshuber, R., et al., "A Comparison Of Strategies To Stabilize Immunoglobulin $F_v$–Fragments" *Biochem.*, 29, 1362–1367 (1990).

Goudsmit, J., et al., "Human Immunodeficiency Virus Type 1 Neutralization Epitope With Conserved Architecture Elicits Early Type–Specific Antibodies In Experimentally Infected Chimpanzees" *Proc. Natl. Acad. Sci. USA* vol. 85, 4478–4482 (Jun. 1988).

Guldner, H.H., et al., "Epitope Mapping With A Recombinant Human 68–kDa (U1) Ribonucleoprotein Antigen Reveals Heterogenous Autoantibody Profiles In Human Autoimmune Sera" *J.Immunol.*, vol. 141, No. 2, 469–475 (Jul. 15, 1988).

Guldner, H.H., et al., "Human Anti–P68 Autoantibodies Recognize A Common Epitope Of U1 RNA Containing Small Nuclear Ribonucleoprotein And Influenza B Virus" *J. Exp. Med.*, vol. 171, 819–829 (Mar. 1990).

Güssow, D., et al., "Humanization Of Monoclonal Antibodies" *Methods Enzymol.*, vol. 203, 99–121 (1991).

Habeshaw, J.A., et al., "AIDS Pathogenesis: HIV Envelope And Its Interaction With Cell Proteins" *Immunol. Today*, 11, 418–425 (1991).

Hamm, J., et al., "In Vitro Assembly Of U1 snRNPs" *EMBO J.*, vol. 6, 3479–3485 (1987).

Hamm, J., et al., "Loop I Of U1 Small Nuclear RNA Is The Only Essential RNA Sequence For Binding Of Specific U1 Small Nuclear Ribonucleoprotein Particle Proteins" *Mol. Cell. Biol.*, vol. 8, No. 11, 4787–4791 (Nov. 1988).

Harbers, M., et al., "Suppression Of c–fos Precursor RNA Splicing By The Protein Kinase C Inhibitor H7 [1–(5–isoquinolinesulphonyl)–2–methylpiperazine]" *Biochem. J.* 278, 305–308 (1991).

Hilvert, D., et al., "Antibody Catalysis Of Concerted, Carbon—Carbon Bond–Forming Reactions" *Methods Enzymol.*, vol. 203, 352–369 (1991).

Hockensmith, J.W., et al., "Laser Cross–Linking Of Nucleic Acids To Proteins" *J. Biol. Chem.*, vol. 261, No. 8, 3512–3518 (Mar. 15, 1986).

Huston, J.S., et al., "Protein Engineering Of Antibody Binding Sites: Recovery Of Specific Activity In An Anti–Digoxin Single–Chain Fv Analogue Produced In *Escherichia coli*" *Proc. Natl. Acad. Sci. USA*, vol. 85, 5879–5883 (Aug. 1988).

Huston, J.S., et al., "Protein Engineering Of Single–Chain Fv Analogs And Fusion Proteins" *Methods Enzymol.*, vol. 203, 46–87 (1991).

Janda, K.D., et al., "Bait And Switch Strategy For Obtaining Catalytic Antibodies With Acyl–Transfer Capabilities" *J. Am. Chem. Soc.*, 112, 1274–1275 (1990).

Javaherian, K., et al., "Principal Neutralizing Domain Of The Human Immunodeficiency Virus Type 1 Envelope Protein" *Proc. Natl. Acad. Sci. USA*, vol. 86, 6768–6722 (Sep. 1989).

Jones, P.T., et al., "Replacing the Complementarity–Determining Regions In A Human Antibody With Those From A Mouse" *Nature*, vol. 321, 522–525 (May 29, 1988).

Kamine, J., et al., "Sp1–Dependant Activation Of A Synthetic Promoter By Human Immunodeficiency Virus Type 1 Tat Protein" *Proc. Natl. Acad. Sci. USA*, vol. 88, 8510–8514 (Oct. 1991).

Karplus, P.A., et al., "Refined Structure Of Glutathione Reductase At 1.54 Å Resolution" *J. Mol. Biol.*, 195, 701–729 (1987).

Kastner, B., et al., "Electron Microscopy Of U1 Small Nuclear Ribonucleoprotein Particles: Shape Of The Particle And Position Of The 5/RNA Terminus" *EMBO J.*, vol. 8, No. 1, 277–286 (1989).

Krainer, A.R., et al., "Functional Expression Of Cloned Human Splicing Factor SF2: Homology To RNA–Binding Proteins, U1 70K, And Drosophila Splicing Regulators" *Cell*, vol. 66, 383–394 (Jul. 26, 1991).

Kreig, A.M., et al., "Expression Of An Endogenous Retroviral Transcript Is Associated With Murine Lupus" *Arthritis and Rheumatism*, vol. 32 No. 3, 322–329, (Mar. 1989).

Kurata, A., et al., "Production Of A Monoclonal Antibody To A Membrane Antigen Of Human T–Cell Leukaemia Virus (HTLV1/ATLV)–Infected Cell Lines From A Systemic Lupus Erythematosus (SLE) Patient: Serological Analyses For HTLV1 Infections In SLE Patients" *Clin. Exp. Immunol.*, vol. 62, 65–74 (1985).

Kyte, J., et al., "A Simple Method For Displaying The Hydropathic Character Of A Protein" *J. Mol. Biol.*, 157, 105–132 (1982).

Laman, J.D., et al., "Variant-Specific Monoclonal And Group-Specific Polyclonal Human Immunodeficiency Virus Type 1 Neutralizing Antibodies Raised With Synthetic Peptides From The gp120 Third Variable Domain" *J. Virol.*, vol. 66, No. 3, 1823–1831 (Mar. 1992).

LaRosa, G.J., et al., "Conserved Sequence And Structural Elements In The HIV-1 Principal Neutralizing Determinant" *Science*, vol. 249, 932–935 (Aug. 24, 1990).

LaRosa, G.J., et al., "Conserved Sequence And Structural Elements In The HIV-1 Principal Neutralizing Determinant: Corrections And Clarifications" *Science*, vol. 251, 811 (Feb. 15, 1991).

LaRosa, G.J., et al., "Conserved Sequence And Structural Elements In The HIV-1 Principal Neutralizing Determinant: Further Clarifications" *Science*, vol. 253, 1146 (1991).

Leonard, C.K., et al., "Assignment Of Intrachain Disulfide Bonds And Characterization Of Potential Glycosylation Sites Of The Type 1 Recombinant Human Immunodeficiency Virus Envelope Glycoprotein (gp120) Expressed In Chinese Hamster Ovary Cells" *J. Biol. Chem.*, vol. 265, No. 18, 10373–10382 (Jun. 25, 1990).

Lerner, M.R., et al., "Antibodies To Small Nuclear RNAs Complexed With Proteins Are Produced By Patients With Systemic Lupus Erythematosus" *Proc. Natl. Acad. Sci. USA*, vol. 76, No. 11, 5495–5499 (Nov. 1979).

Lerner, M.R., et al., "Are snRNPs Involved in Splicing?" *Nature*, vol. 283, 220–224 (Jan. 1980).

Lutz–Freyermuth, C., et al., "Quantitative Determination That One Of Two Potential RNA–Binding Domains Of The A Protein Component Of The U1 Small Nuclear Ribonucleoprotein Complex Binds With High Affinity To Stem–Loop II Of U1 RNA" *Proc. Natl. Acad. Sci. USA*, vol. 87, 6393–6397 (Aug. 1990).

Maizel, J.V., et al., "Enhanced Graphic Matrix Analysis Of Nucleic Acid And Protein Sequences" *Proc. Natl. Acad. Sci. USA*, vol. 78, No. 12, 7665–7669 (Dec. 1981).

Maul, G.G., et al., "Determination Of An Epitope Of The Diffuse Systemic Sclerosis Marker Antigen DNA Topoisomerase I: Sequence Similarity With Retroviral p30$^{gag}$ Protein Suggests A Possible Cause For Autoimmunity In Systemic Sclerosis" *Proc. Natl. Acad. Sci. USA*, vol. 86, 8492–8496 (Nov. 1989).

McCune, J.M., et al., "Endoproteolytic Cleavage of gp160 Is Required For the Activation Of Human Immunodeficiency Virus" *Cell*, vol. 53, 55–67 (Apr. 8, 1988).

Merrill, B.M., et al., "Photochemical Cross–Linking Of The *Escherichia coli* Single–Stranded DNA–Binding Protein To Oligodeoxynucleotides" *J. Biol. Chem.*, vol. 259, No. 17, 10850–10856 (Sep. 10, 1984).

Merrill, B.M., et al., "Phenylalanines That Are Conserved Among Several RNA–Binding Proteins Form Part Of A Nucleic Acid–Binding Pocket In The A1 Heterogeneous Nuclear Ribonucleoprotein" *J. Biol. Chem.*, vol. 263, No. 7, 3307–3313 (Mar. 5, 1988).

Modrow, S., et al., "Computer–Assisted Analysis Of Envelope Protein Sequences Of Seven Human Immunodeficiency Virus Isolates: Prediction Of Antigenic Epitopes In Conserved And Variable Regions" *J. Virol.*, vol. 61, No. 2, 570–578 (Feb. 1978).

Nara, P.L., et al., "Simple, Rapid, Quantitative, Syncytium-–Forming Microassay For The Detection Of Human Immunodeficiency Virus Neutralizing Antibody" *AIDS Res. Hum. Retro.* 3, 283–302 (1987).

Okamoto, T., et al., "Evidence In Patients With Systemic Lupus Erythematosus Of The Presence Of Antibodies Against RNA–Dependent DNA Polymerase Of Baboon Endogenous Virus" *Clin. exp. Immunol.* 54, 747–755 (1983).

Oldstone M.B., "Molecular Mimicry as a Mechanism for the Cause and as a Probe Uncovering Etiologic Agent(s) of Autoimmune Disease" *Current Topics in Microbiology and Immunology* vol. 145, 127–135 (1989).

Oldstone, M.B.A., et al., "Mapping The Anatomy Of The Immunodominant Domain Of The Human Immunodeficiency Virus gp41 Transmembrane Protein: Peptide Conformation Analysis Using Monoclonal Antibodies And Proton Nuclear Magnetic Resonance Spectroscopy" *J. Virol.*, vol. 65, No. 4, 1727–1734 (Apr. 1991).

Patton, J.R., et al., "Reconstitution Of The U1 Small Nuclear Ribonucleoprotein Particle" *Mol. Cell. Biol.*, vol. 7, No. 11, 4030–4037 (Nov. 1987).

Piñol–Roma, S., et al., "Shuttling Of Pre–mRNA Binding Proteins Between Nucleus And Cytoplasm" *Nature*, vol. 355, 730–732 (Feb. 20, 1992).

Prujin, G.J.M., et al., "Inhibition Of Adenovirus DNA Replication In Vitro By Autoimmune Sera" *Eur. J. Biochem.*, 154, 363–370 (1986).

Putney, S.D., et al., "HTLV–III/LAV—Neutralizing Antibodies to an *E. coli*—Produced Fragment Of The Virus Envelope" *Science*, vol. 234, 1392–1395 (Dec. 12, 1986).

Query, C.C., et al., "A Common RNA Recognition Motif Identified Within A Defined U1 RNA Binding Domain Of The 70K U1 snRNP Protein" *Cell*, vol. 57, 89–101 (Apr. 7, 1989).

Query, C.C., et al., "A Specific 31–Nucleotide Domain Of U1 RNA Directly Interacts With The 70K Small Nuclear Ribonucleoprotein Component" *Mol. Cell. Biol.*, vol. 9, No. 11, 4872–4881 (Nov. 1989).

Reuter, R., et al., "Immunization Of Mice With Purified U1 Small Nuclear Ribonucleoprotein (RNP) Induces A Pattern Of Antibody Specificities Characteristic Of The Anti–Sm And Anti–RNP Autoimmune Response Of Patients With Lupus Erythematosus, As Measured By Monoclonal Antibodies" *Proc. Natl. Acad. Sci. USA*, vol. 83, 8689–8693 (1986).

Riechmann, L., et al., "Reshaping Human Antibodies For Therapy" *Nature*, vol. 332, 323–327 (Mar. 24, 1988).

Robert–Guroff, M., et al., "HTLV–III—Neutralizing Antibodies In Patients With AIDS And AIDS–Related Complex" *Nature*, vol. 316, 72–74 (Jul. 4, 1985).

Rucheton, M., et al., "Presence Of Circulating Antibodies Against gag–Gene MuLV Proteins In Patients With Autoimmune Connective Tissue Disorders" *Virology*, 144, 468–480 (1985).

Rusche, J.R., et al., "Antibodies That Inhibit Fusion Of Human Immunodeficiency Virus–Infected Cells Bind A 24–Amino Acid Sequence Of The Viral Envelope, gp120" *Proc. Natl. Acad. Sci. USA*, vol. 85, 3198–3202 (May 1988).

Schwimmbeck, P.L., et al., "Autoantibodies To HLA B27 In The Sera Of HLA B27 Patients With Ankylosing Spondylitis And Reiter's Syndrome" *J. Exp. Med.*, vol. 166, 173–181 (Jul. 1987).

Shokat, K.M., et al., "Catalytic Antibodies" *Methods Enzymol.*, vol. 203, 327–351 (1991).

Singer, B.S., et al., "Phage T4 Expression Vector: Protection From Proteolysis" *Gene*, 106, 1–6 (1991).

Skinner, M.A., et al., "Characteristics Of A Neutralizing Monoclonal Antibody To The HIV Envelope Glycoprotein" *AIDS Res. Hum. Retro.*, vol. 4, No. 3, (1988).

Surowy, C.S., et al., "Direct, Sequence–Specific Binding Of The Human U1–70K Ribonucleoprotein Antigen Protein To Loop I Of U1 Small Nuclear RNA" *Mol. Cell. Biol.*, vol. 9, No. 10, 4179–4186 (Oct. 1989).

Tai, M–S., et al., "A Bifunctional Fusion Protein Containing Fc–Binding Fragment B Of Staphylococcal Protein A Amino Terminal To Antidigoxin Single–Chain Fv" *Biochem.* 29, 8024–8030 (1990).

Theissen, H., et al., "Cloning Of The Human cDNA For The U1 RNA–Associated 70K Protein" *EMBO J.*, vol. 5, No. 12, 3209–3217 (1986).

Thomas, D.J., et al., "gp160, The Envelope Glycoprotein Of Human Immunodeficiency Virus Type 1, Is A Dimer Of 125–Kilodalton Subunits Stabilized Through Interactions Between Their gp41 Domains" *J. Virol.*, vol. 65, No. 7, 3797–3803 (Jul. 1991).

Von Ahsen, U., et al., "Antibiotic Inhibition Of Group I Ribozyme Function" *Nature*, vol. 353, 368–370 (Sep. 26, 1991).

Woppman, A., et al., "Direct Cross–Linking Of snRNP Protein F And 70K To snRNAs By Ultra–Violet Radiation In Situ" *Nuc. Acid Res.*, vol. 16, No. 23, 10985–11004 (1988).

Johnson, S., et al., "Construction Of Single–Chain Fv Derivatives Of Monoclonal Antibodies and Their Production In *Escherichia coli*" *Methods Enzymol.*, vol. 203, 88–98 (1991).

Noller, H.F., "Drugs And The RNA World" *Nature*, vol. 353, 302–303 (Sep. 26, 1991).

FIG. 2A

```
U₁snRNP 70K    61 GIE GERLDRRKERRRQUEALIEDQQQRQ  98 PGRAASSAGIGGRQGLL  124 SGLVRSSSGR  142 SSSGR  159 PRASGQTPER
HIV-1 GP120/41 732 GIEEEGERDRDRSIR  645 LIEESQNQQ  319 PGRAFVTIG  595 QLLG  440 SGQIRCSS  844 PRRI

```
HIV-1 GP120/41   ...RGP|G R|A F V|T I G|K...
    hnRNP A2/B1  ...KKR|G F|Q F V|T F D|D...
       hnRNP A1  ...KKR|G F|A F V|T F D|D...
    U₁snRNP 70K  ...KPR|G Y|A F I|E Y E|H...
      U₁snRNP A  ...KAR|G Q|A F V|I F K|E...
     U₁snRNP B1  ...KMR|G Q|A F V|I F K|E...
      fly sxl 2  ...RPR|G V|A F V|R Y N|K...
```

FIG. 2B

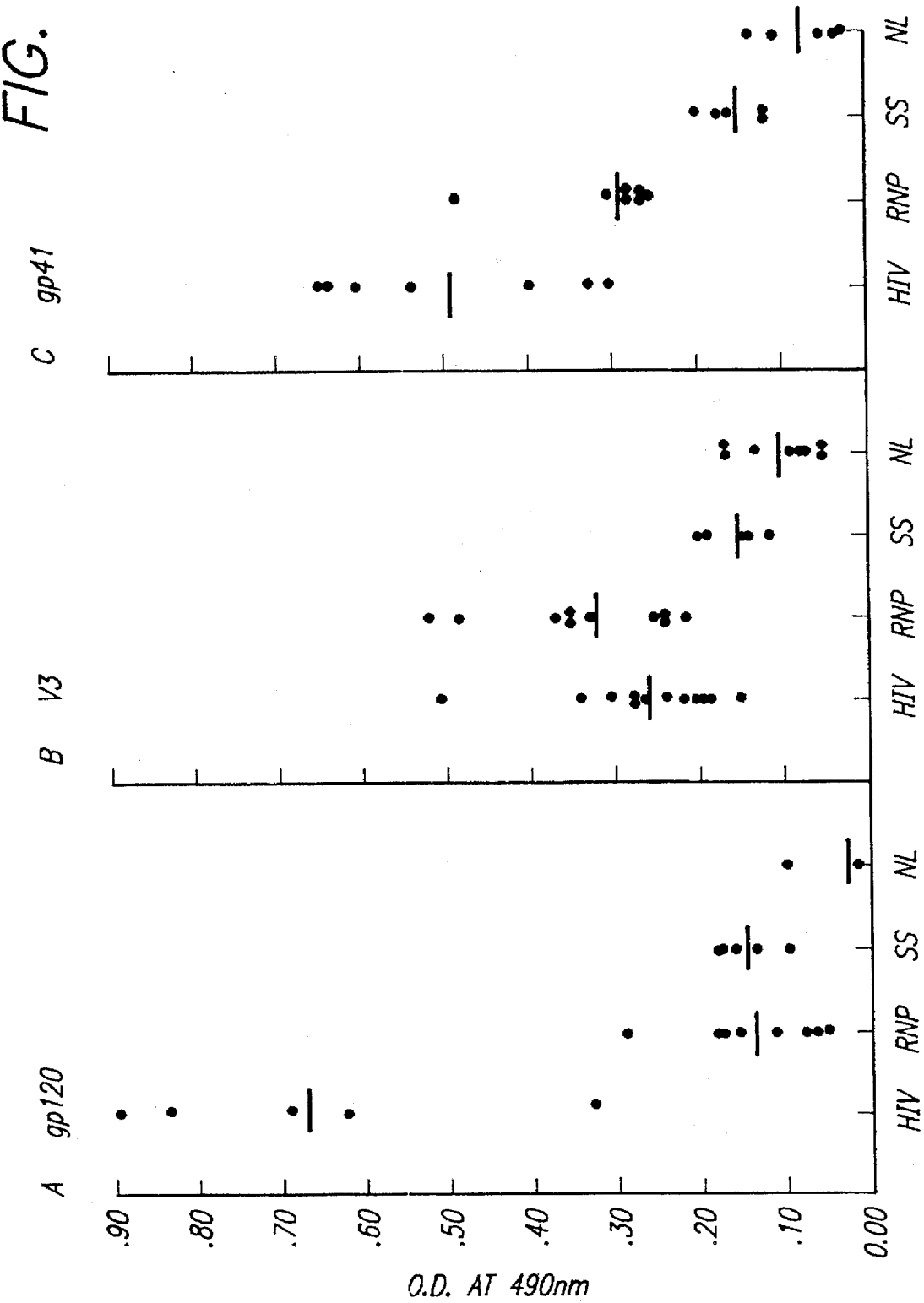

५,७०७,६२६

METHODS OF TREATING HIV INFECTION USING ANTIBODIES TO THE U2 SMALL NUCLEAR RIBONUCLEAR PROTEIN

This application is a continuation of U.S. application Ser. No. 08/029,850, filed Mar. 11, 1993, now abandoned.

BACKGROUND OF THE INVENTION

The present invention relates generally to the fields of biochemistry and medicine. In particular, the present invention relates to therapeutic strategies for the treatment of immunoinfective cluster virus infections.

Disease expression in systemic rheumatic disorders (SRDs) has several features in common with infections caused by immunoinfective cluster viruses (ICVs)—e.g. human immunodeficiency virus 1 (HIV-1), herpes simplex virus 1 (HSV-1) and other immunoinfective adenoviruses, human lymphotropic retroviruses (e.g., HTLV-1), rubella virus, cytomegalovirus (CMV), and Epstein-Barr virus (EBV). Common immune anomalies include lymphokine dysregulation, polyclonal B-cell activation, autoantibody production, anergy, diminished responses to specific antigens, and altered ratios of $CD4^+$ to $CD8^+$ T lymphocytes. Common clinical similarities include a subacute, exacerbating, and remitting course; inflammation; musculoskeletal complaints; and lymphadenopathy.

Efforts to demonstrate a viral etiology for SRDs have, heretofore, produced inconclusive results. [R. Fox "Epstein-Barr Virus and Human Autoimmune Diseases: Possibilities and Pitfalls" *J. Virol. Methods* 21, 19–27 (1988)]. Accumulated data on cross-reactivities between SRD antibodies and viruses demonstrate that sera from patients with a single disorder react with viruses of different families. [Fox, "supra"; A. M. Krieg et al. "Expression of an Endogenous Retroviral Transcript is Associated with Murine Lupus" *Arthritis Rheum.* 32, 322–329 (1989)]. Two examples are systemic lupus erythematosus (SLE), characterized by high titer autoantibodies to U1, U2, and U4 to U6 small nuclear ribonucleoprotein (snRNP) particles [M. R. Lerner et al. "Antibodies to Small Nuclear RNAs Complexed with Proteins are Produced by Patients with Systemic Lupus Erythematosus" *Proc. Natl. Acad. Sci. USA* 76, 5494–5499 (1979); E. H. Schumacher "Primer on the Rheumatic Diseases" (Arthritis Found., Atlanta), 9th Ed. (1988)], and scleroderma, in which 40–50% of patients have antibodies to centromeres, and another 25–30% have antibodies to Scl-70 (scleroderma 70-kDa antigen)/topoisomerase I [Schumacher, "supra"]. Antibodies in SLE sera have been found to cross-react with the retroviruses human T-cell lymphotropic virus type I and murine leukemia virus, and the DNA viruses EBV and CMV. [A. Kurata et al. "Production of a Monoclonal Antibody to a Membrane Antigen of Human T-cell Leukaemia Virus (HTLV1/ATLV)-infected Cell Lines from a Systemic Lupus Erythematosus (SLE) Patient: Serological Analyses for HTLV1 Infections in SLE Patients" *Clin. Exp. Immunol.* 62, 65–74 (1985); M. Rucheton et al. "Presence of Circulating Antibodies Against Gag-Gene MuLV Proteins in Patients with Autoimmune Connective Tissue Disorders" *Virology* 144, 468–480 (1985); T. Okamoto et al. "Evidence in Patients with Systemic Lupus Erythematosus of the Presence of Antibodies Against RNA-Dependent DNA Polymerase of Baboon Endogenous Virus" *Clin. Exp. Immunol.* 54, 747–755 (1983)]. Both scleroderma and SLE sera inhibit replication of the same adenoviral strains in vitro. Furthermore, antibodies to a single virus—e.g., EBV—occur in several disorders, including SLE, Sjogren syndrome, and rheumatoid arthritis [R. I. Fox, et al. "Potential Role of Epstein-Barr Virus in Sjögren's Syndrome" *Rheum. Dis. Clin. North Am.* 13, 275–292 (1987); Fox, "supra", G. J. Pruijin "Inhibition of Adenovirus DNA Replication in vitro by Autoimmune Sera" *Eur. J. Biochem.* 154, 363–370 (1986)].

A recent approach to establishing a viral link has involved the search for amino acid sequence homologies between major nuclear antigens and viral proteins. This approach is based on bacterial/autoimmune paradigms, in which molecular mimicry is believed to generate anti-self antibodies which injure cells and tissues [M. B. Oldstone et al. "Concepts in Viral Pathogenesis" (Springer, N.Y.) Vol. 2, 195–202 (1984)]. An example is the identification of common epitopes between Klebsiella nitrogenase reductase and HLA B27.1, which carries an increased risk for ankylosing spondylitis [A. Catin et al. "Genetic Differences Between B27 Positive Patients with Ankylosing Spondylitis and B27 Positive Healthy Controls" *Arthritis Rheum.* 26, 1460–1464 (1983); P. L. Schcuimmbeck et al. "Autoantibodies to HLA B27 in the Sera of HLA B27 Patients with Ankylosing spondylitis and Reiter's Syndrome" *J. Exp. Med.* 166, 173–181 (1987); P. J. Bjorkman et al. "The Foreign Antigen Binding Site and T Cell Recognition Regions of Class I Histocompatibility Antigens" *Nature* 329, 512–518 (1987); C. Ewing et al. "Antibody Activity in Ankylosing Spondylities Sera to Two Sites on HLA B27.1 at the MHC Groove Region (Within Sequence 65–85), and to a Klebsiella Pneumoniae Nitrogenase Reductase Peptide (Within Sequence 181–199)" *J. Exp. Med.* 171, 1635–1647 (1990)]. Recently viral homologies have been reported in two major nuclear antigens: Scl-70/topoisomerase I [G. G. Maul et al. "Determination of an Epitope of the Diffuse Systemic Sclerosis Marker Antigen DNA Topoisomerase I: Sequence Similarity with Retroviral $p30^{gag}$ Protein Suggests a Possible Cause for Autoimmunity in Systemic Sclerosis" *Proc. Natl. Acad. Sci. USA* 86, 8492–8496 (1989)], and the 70-Kda antigen, a component of U1 RNP particles [C. C. Query et al. "A Common RNA Recognition Motif Identified within a Defined U1 RNA Binding Domain of the 70K U1 snRNP Protein" *Cell* 51, 211–220 (1987); H. H. Guldner et al. "Human Anti-P68 Autoantibodies Recognize a Common Epitope of U1 RNA Containing Small Nuclear Ribonucleoprotein and Influenza B Virus" *J. Exp. Med.* 171, 819–829 (1990)]. Interestingly, two homologies identified by different investigators in the 70-Kda protein are each associated with a different virus: a type C retrovirus [Query et al., "supra"] and influenza B virus [Guldner et al., "supra"].

AIDS (acquired immunodeficiency syndrome) is caused by HIV-1, in apparent synergy with other immunoinfective viruses, including HSV-1, CMV and EBV [J. M. Gimble et al. "Epitope Mapping with a Recombinant Human 68-Kda (U1) Ribonucleoprotein Antigen Reveals Heterogeneous Autoantibody Profiles in Human Autoimmune Sera" *J. Immunol.* 141, 469–475 (1988); J. Kamine et al. "Sp1-Dependent Activation of a Synthetic Promoter by Human Immunodeficiency Virus Type 1 Tat Protein" *Proc. Natl. Acad Sci. USA* 88, 8510–8514 (1991); M. A. Albrecht et al. "The Herpes Simplex Virus Immediate—Early Protein, ICP4, Is Required to Potentiate Replication of Human Immunodeficiency Virus in $CD4^+$ Lymphocytes" *J. Virol.* 63, 1861–1868 (1989)]. Key structural and regulatory proteins in all four viruses have sequences in common with nuclear elements reacting with autoantibodies in the human disorder, mixed connective tissue disease (MCTD) [A. Douvas et al. "Multiple Overlapping Homologies Between Two Rheumatoid Antigens and Immunosuppressive Viruses"

Proc. Natl. Acad. Sci. USA 88, 6328–6332 (1991)]. One of these nuclear elements is U1 snRNP, belonging to the set of small ribonucleoprotein complexes (including also U2 and U4–6 snRNP) which splice precursor mRNA [P. Bringmann et al. "Purification of the Individual snRNPs U1, U2, U5 and U4/U6 from HeLa Cells and Characterization of their Protein Constituents" EMBO J. 5, 3509–3516 (1986); S. M. Berget et al. "U1, U2, and U4/U6 Small Nuclear Ribonucleoproteins are Required for in Vitro Splicing but not Polyadenylation" Cell 46, 691–696 (1986)]. In the U1 snRNP, the distinctive RNA core is associated with four polypeptides, including 70K, which are antigenic in MCTD [R. Reuter et al. "Immunization of Mice with Purified U1 Small Nuclear Ribonucleoprotein (RNP) Induces a Pattern of Antibody Specificities Characteristic of the Anti-Sm and Anti-RNP Autoimmune Response of Patients with Lupus Erythematosus, as Measured by Monoclonal Antibodies" Proc. Natl. Acad. Sci. USA 83, 8689–8693 (1986)]. The U1 RNA, though weakly antigenic itself, binds the polypeptides into a potently immunoprecipitating complex [A. S. Douvas et al. "Isolation and Characterization of Nuclear Ribonucleoprotein Complexes Using Human Anti-Nuclear Ribonucleoprotein Antibodies" J. Biol. Chem. 254, 3608–3616 (1979)].

The 70K protein, the only protein in the complex with extensive homologies to immunoinfective viruses, has six exact homologies of $\geq 5$ amino acids in common with the envelope sequences of HIV-1, and eight in common with HSV-1 [Douvas et al., "supra" (1991), (incorporated herein by reference)].

The HIV-1 envelope glycoprotein complex gp120/41 is derived from a gp160 precursor by proteolytic cleavage [J. M. McClune et al. "Endoproteolytic Cleavage of gp160 is Required for the Activation of Human Immunodeficiency Virus" Cell 53, 55–67 (1988)]. The surface moiety gp120 has five structural domains [S. Modrow et al. "Computer-Assisted Analysis of Envelope Protein Sequences of Seven Human Immunodeficiency Virus Isolates: Prediction of Antigenic Epitopes in Conserved and Variable Regions" J. Virol. 61, 570–578 (1987)]. The V4 domain, whereby the virus attaches to $CD4^+$ T lymphocytes, is not a potent immunogen in animals, and antibodies produced by hybridoma technology lack the avidity to compete effectively with binding of the virus to T cells [J. A. Habeshaw et al. "AIDS Pathogenesis: HIV Envelope and its Interaction with Cell Proteins" Immunol. Today 11, 418–425 (1991)]. In contrast, the V3 loop is a potent immunogen [Laman et al., "supra"; P. A. Broliden et al. "Identification of Human Neutralization-Inducing Regions of the Human Immunodeficiency Virus Type 1 Envelope Glycoproteins" Proc. Natl. Acad. Sci. USA 89, 461–465 (1992)]. It dominates the virus in generating antibodies which inhibit (neutralize) the virus in cell culture assays, and is the focus of efforts to develop immunoprotective vaccines [J. Goudsmit et al. "Human Immunodeficiency Virus Type 1 Neutralization Epitope With Conserved Architecture Elicits Early Type-Specific Antibodies in Experimentally Infected Chimpanzees" Proc. Natl. Acad. Sci. USA 85, 4478–4482 (1988); M. Girard et al. "Immunization of Chimpanzees Confers Protection Against Challenge with Human Immunodeficiency Virus" Proc. Natl. Acad. Sci USA 88, 542–546 (1991); S. D. Putney et al. "HTLV-III/LAV-Neutralizing Antibodies to an E. coli-Produced Fragment of the Virus Envelope" Science 234, 1392–1395 (1986)]. However, despite having anti-V3 antibodies which neutralize in vitro, AIDS victims succumb to the disease for reasons which are not hay understood, but may include insufficient titers of antibodies [M. Robert-Guroff et al. "HTLV-III-Neutralizing Antibodies in Patients with AIDS and AIDS-Related Complex" Nature 316, 72–74 (1985).

Multiple viruses interact to produce immune anomalies in infected individuals, and generate epitopes cross-reacting with autoantibodies in SRDs [Douvas et al., "supra" (1991)]. It would, therefore, be advantageous to develop novel therapeutic strategies for the treatment of immunoinfective cluster viruses infections based on autoantibodies reacting with these homologous amino acid sequences.

SUMMARY OF THE INVENTION

In accordance with a first aspect of the present invention, there is provided a method of treating immunoinfective cluster virus infections in humans involving administration to a patient infected by said virus, serum or plasma isolated from at least one individual having antibodies characteristic of autoantibodies produced by patients affected with systemic rheumatic disorders.

In accordance with another aspect of the present invention, there is provided a method of treating immunoinfective cluster virus infections in humans involving the use of at least one monoclonal antibody or fraction thereof which is directed against the same or similar epitopes as autoantibodies produced by patients affected with systemic rheumatic disorders.

In accordance with another aspect of the present invention, there is provided a method of treating immunoinfective cluster virus infections in humans involving administration to a patient in need thereof, U1 RNA or fragments thereof.

In accordance with another aspect of the present invention, there is provided a method of treating immunoinfective cluster virus infections in humans involving administration to a patient in need thereof RNA splicing inhibitors.

In accordance with yet another aspect of the present invention, there is provided a method of treating immunoinfective cluster virus infections in humans involving administration of a combination of any of the foregoing therapeutic agents.

BRIEF DESCRIPTION OF THE DRAWINGS

FIGS. 2A and 2B illustrate the amino acid sequence homologies between U1 snRNP 70K and gp120/41 relating to the epitope domains of 70K and the U1 consensus binding sequences.

DETAILED DESCRIPTION OF THE INVENTION

Figure 1A:
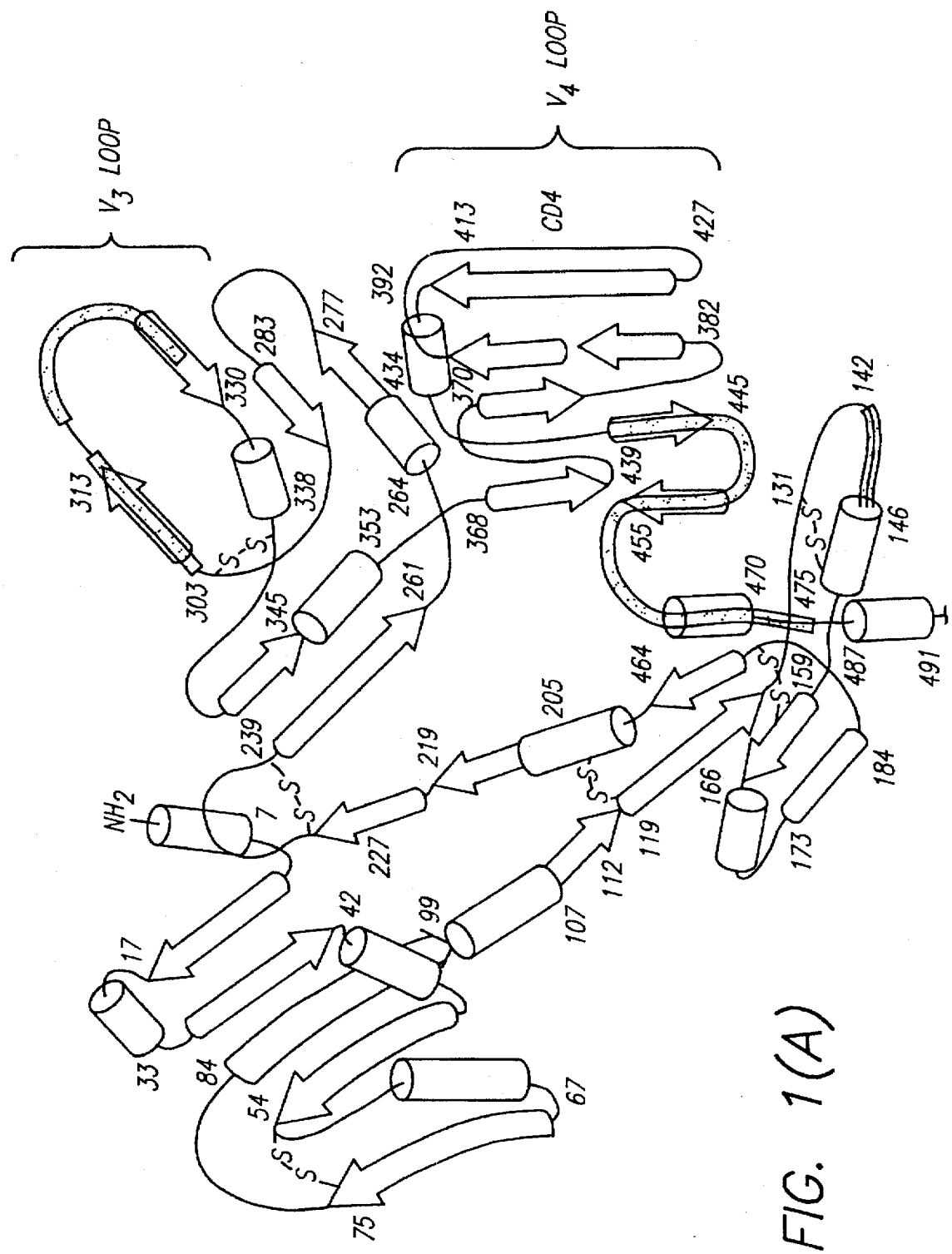
FIG. 1 is a computer-assisted model of HIV-1 surface protein complex gp120/41 with superimposed homologies to U1 snRNP 70K.

Use of Sera from Patients with SRDs

Immunoinfective cluster viruses contain specific sequence forms which are recognized as epitopes which are important in viral infectivity and therefore in anti-viral defense. Additionally, certain normal human proteins, which coincidentally contain the same or similar epitopes as the ICV epitopes mentioned hereinabove, are the targets of potent autoantibodies. These autoantibodies occur in high titers in patients suffering from any one of a cluster of autoimmune syndromes known as systemic rheumatic disorders or SRDs. These autoimmune antibodies cross-react with viral epitopes.

The autoimmune conditions of primary interest in this application are classified as systemic rheumatic disorders (SRDs), and are listed in Table I. In addition to these primary disorders, there are a number of associated conditions, also listed in Table I. The SRDs are characterized by the production of autoantibodies reacting primarily with molecules localized in cell nuclei. Hence the target molecules are referred to generically as nuclear antigens, and are of several specific types (Table I). The antibodies are generically referred to as anti-nuclear antibodies, although all have more specific descriptors. It is important to note that each nuclear antigen consists of one or more polypeptide chains, may also include nucleic acids, and has multiple epitopes.

The nuclear protein antigens listed in Table I are asymmetric, with very hydrophilic sequences concentrated in discrete domains. These domains are usually asymmetrically located at either the $NH_2$ or COOH-end of the protein, with non-polar sequences at the opposing end. The hydrophilic domains are of three types, namely alternating acidic/basic, purely acidic and purely basic. The alternating acidic/basic sequences are characterized in that the acidic amino acid residues, aspartic and/or glutamic acids (symbols D and E, respectively), alternate with the basic residues, arginine and/or lysine (symbols R and K, respectively). Exemplary but not limiting examples of such alternating acidic/basic sequences are the RDRDRDR SEQ ID NO:1, RERERERE-RERE SEQ ID NO:2 and variations thereof such as RREER-REE . . . SEQ ID NO:3, RRERRE SEQ ID NO:4, and the like, and KEKEKEK SEQ ID NO:5 sequences. Exemplary but not limiting examples of the purely acidic sequences are the EEEEEE SEQ ID NO:6, EDDEEDEDE SEQ ID NO:7 and DDDDDD SEQ ID NO:8 sequences. Exemplary but not limiting examples of the purely basic sequences are the RRRRRR SEQ ID NO:9, RKRKRKK SEQ ID NO:10, and KKKKKKK SEQ ID NO:11 sequences.

In addition to being recognizable for extreme hydrophilicity, as in the examples shown above, or for having a regular pattern of alternation of acidic or basic residues, the sequences which react with antibodies described in this application also occur in patterns called "motifs". A motif is a sequence with a recognizable characteristic (such as, for example, a composition of glutamic acid and arginine). This pattern is recognizable, and occurs in similar, but not necessarily identical forms in other molecules, or other parts of the same molecule. The sequence RDRDRDR SEQ ID NO:1 is an example, occurring in three locations, in varying lengths, in 70K, and also in similar form (ERDRDRD) SEQ ID NO:12 in gp41 of HIV-1 (see Table II). Another example is the RERRR SEQ ID NO:13 motif, also occurring as RRERE SEQ ID NO:14 and EREEER SEQ ID NO:15 in 70K (Query et al., "supra"). Additional examples are seen in the acidic domains of the centromere protein CENP-B (see Table III), including the EDDEE SEQ ID NO:16 motif, also occurring as DDDEED SEQ ID NO:17, DEEEDDE SEQ ID NO:18, EDEDDD SEQ ID NO:19, and other forms, in the same protein (sequence from W. C. Earnshaw et al. [W. C. Earnshaw et al. "Molecular cloning of cDNA for CENP-B, the major human centromere autoantigen." J. Cell. Biol. 104: 817–829 (1987) ]). The importance of these motifs is that they are shared by both immune cluster viruses and autoantigens (Tables II and III), and are epitopes for autoantibodies occurring in SRDs.

Immunoinfecting cluster viruses are known to act synergistically in infecting the immune system. Numerous hydrophilic domains have been identified which are present in both the viruses and nuclear antigens. Table II (from A. Douvas et al. [Douvas et al., "supra" (1991)]) depicts the occurrence of exact homologies between the 70K nuclear antigen and the gp 120/41 of HIV-1 as well as similarities between 70K and the synergizing viruses HSV-1, CMV and EBV.

Of particular interest are a number of homologies between the amino acid sequence of 70K and amino acid sequences corresponding to the immediate early (I.E.) and early functions of HSV-1 and CMV. These functions are believed to be not only synergistic, but essential for activating regulatory functions in HIV-1, such as those encoded by long terminal repeats (LTR). [J. M. Gimble et al. "Activation of the Human Immunodeficiency Virus Long Terminal Repeat by Herpes Simplex Virus Type 1 is Associated with Induction of a Nuclear Factor That Binds to the NF-$_k$B/Core Enhancer Sequence" J. Virol. 62, 4104–4112 (1988); Kamine et al., "supra"; Albrecht et al. "supra"]

Figure 7A:
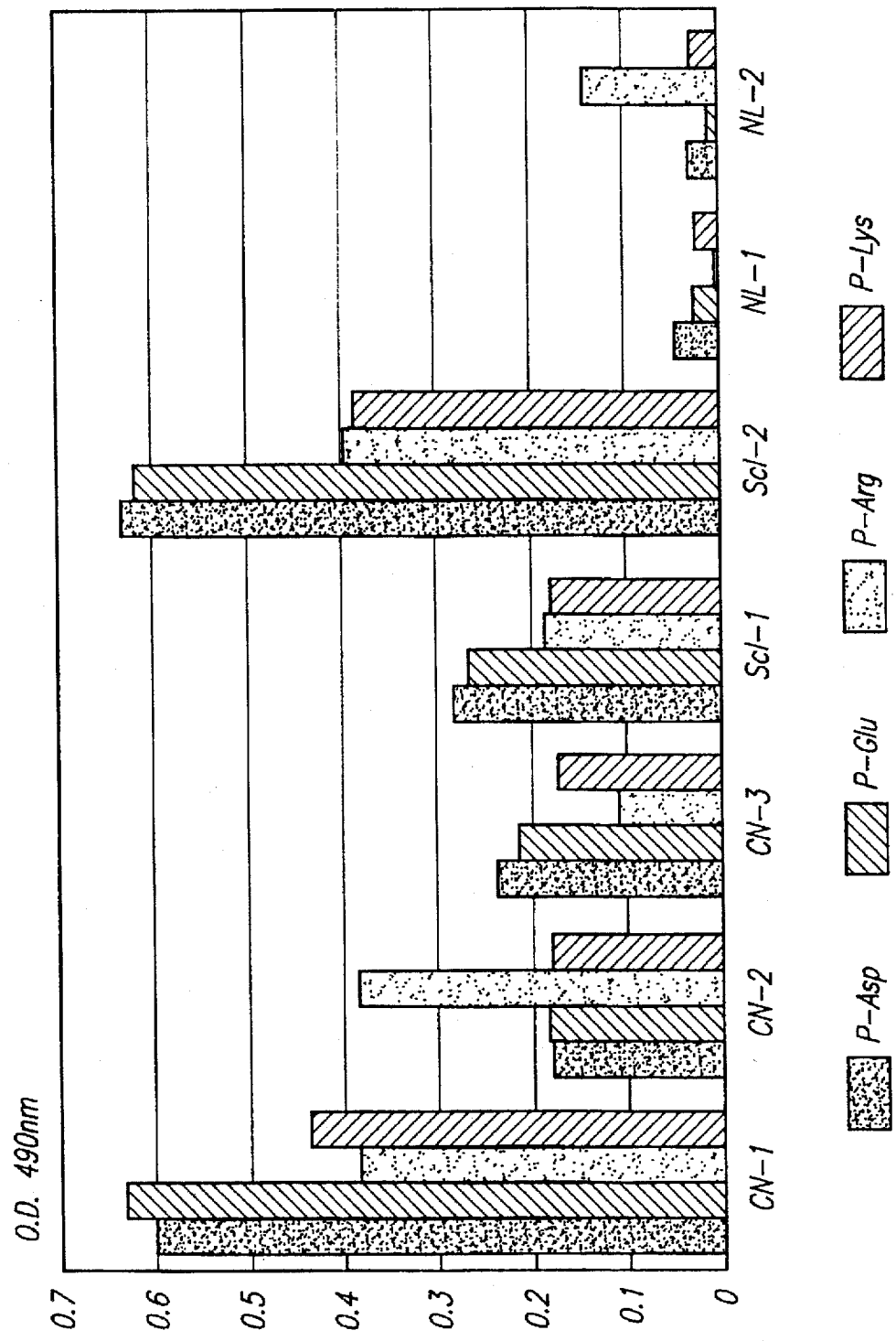
FIG. 7A and B show ELISA reactivities of anti-centromere, anti-Scl-70, anti-RNP and normal sera to synthetic peptides.
Figure 7B:
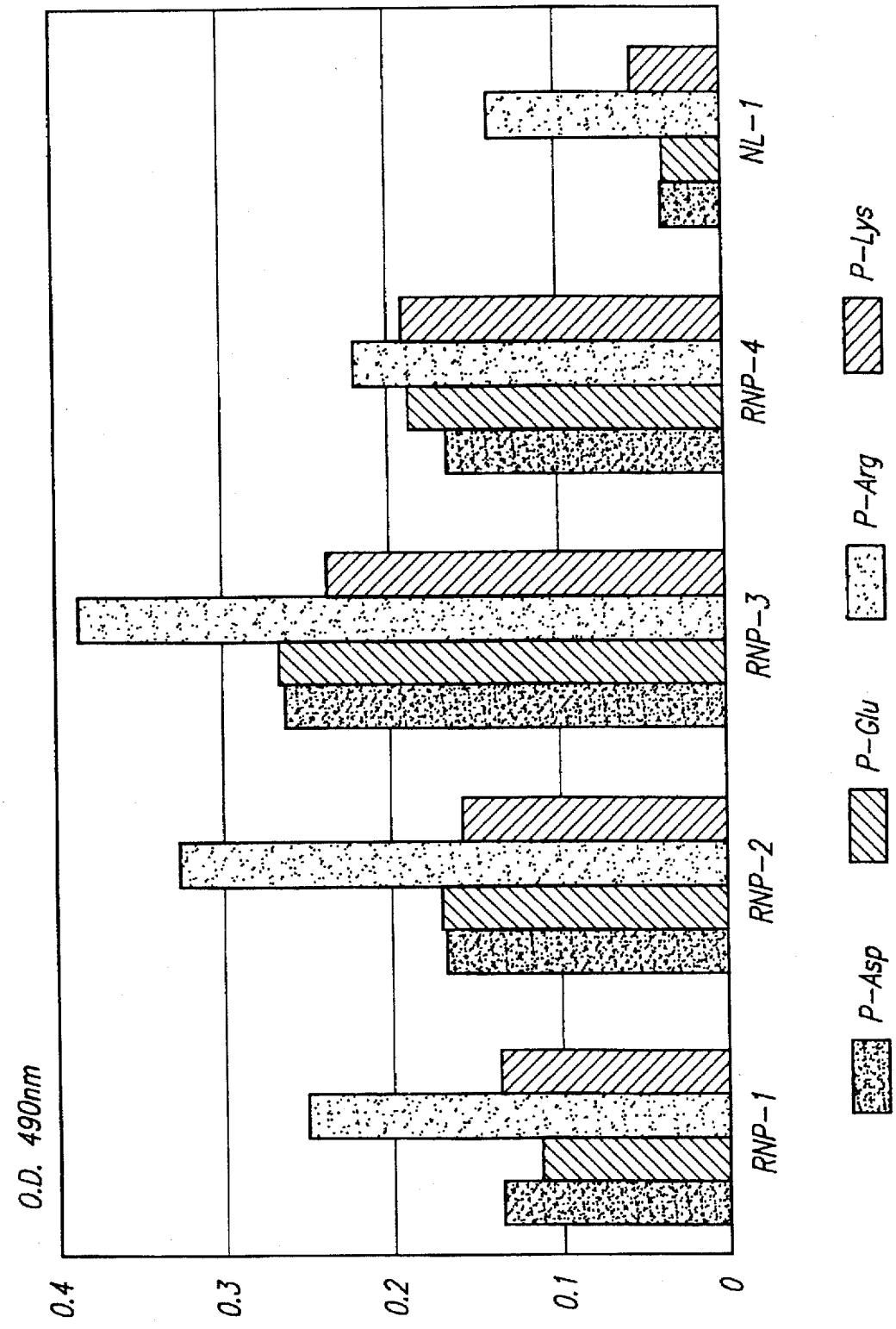

A number of homologies exist between ICV proteins including those belonging to HSV-1 and HIV-1 and another major antigen in SRDs the centromere protein CENP-B, reacting with autoantibodies in scleroderma [Douvas et al., "supra" (1991)]. Table III (from A. Douvas [Douvas et al., "supra" (1991)]) depicts the occurrence of exact homologies between the centromere protein CENP-B and the gp120/41 of HIV-1 as well as similarities between CENP-B and the synergizing viruses HSV-1, CMV and EBV. High titer anti-centromere antibodies occur in approximately 45% of scleroderma patients, unmixed with other specificities [Schumacher et al., "supra"]. Homologies to HIV-1, HSV-1 and CMV are clustered in two extremely hydrophilic domains in CENP-B, composed almost entirely of glutamic acid (domain 1) and aspartic and glutamic acid (domain 2). What is unusual about these domains is their length. Both contain epitopes for scleroderma autoantibodies [W. C. Earnshaw et al. "Molecular Cloning of CDNA for CENP-B, the Major Human Centromere Autoantigen" J. Cell Biol. 104, 817–829 (1987)]. The prediction is made that autoantibodies reacting with domain 1 and 2 epitopes of CENP-B, and with hydrophilic domains in the scleroderma antigen Scl-70 and the MCTD antigen 70K, will react with other polypeptides having hydrophilic domains. This prediction is supported by ELISA data presented in Example 1 (FIGS. 7A and 7B). These figures show reactivity of these antibodies to synthetic substrates of poly-glutamic acid, aspartic acid, lysine and arginine. The data predict strong cross-reactivity of antibodies to the analogous sequences in ICV infections, and therefore therapeutic utility for these antibodies. This prediction is support by ELISA data presented in Example 2

(and FIG. 6), in which anti-RNP sera demonstrate a high reactivity to HSV-1 infected cell lysates. Therefore, sera from SRD patients are useful in the treatment of patients having ICV infections.

Treatment of HIV-1 Infections

Figure 1B:
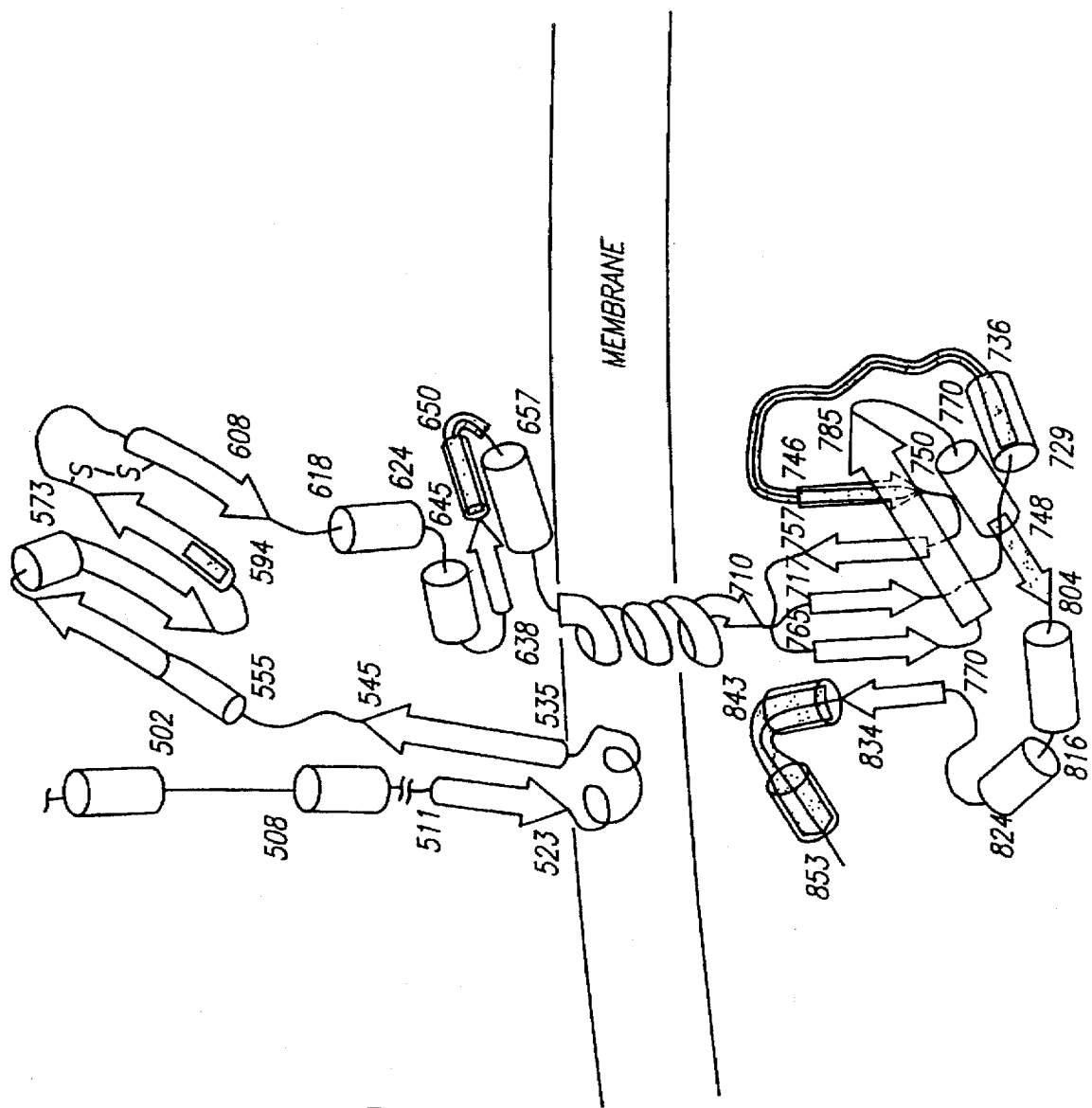

The surface glycoprotein complex of HIV-1 is a bimolecular structure, gp120/41, derived by proteolytic cleavage of a precursor, gp160. As shown in FIG. 1, the gp120 moiety projects on the surface of HIV-1, whereas gp41 is primarily the transmembrane and cytoplasmic component. FIG. 1 is a 2-dimensional rendition of this complex which was constructed by computer modeling of existing chemical data. The CD4 binding site, whereby the virus attached to T "helper" cells, as shown, is in the variable V4 domain of gp120. The V3 domain, as discussed further below (see, FIG. 3) is the primary target of neutralizing antibodies, whereas the V4 loop and CD4 binding site have proven, disappointingly, to be immunologically silent.

In FIG. 1 the HIV-1 DNA sequence (K03455) was obtained from GenBank and translated into the amino acid sequences for gp120 and 41, using a VAX/VMS computer. Disulfide bonds in gp120 were identified by enzymatic cleavage and HPLC [C. L. Leonard et al. "Assignment of Intrachain Disulfide Bonds and Characterization of Potential Glycosylation Sites of the Type 1 Recombinant Human Immunodeficiency Virus Envelope Glycoprotein (gp120) Expressed in Chinese Hamster Ovary Cells" *J. Biol. Chem.* 265, 10373–10382 (1990)]. The disulfide bond between residues 598–604 in gp41 was identified by NMR [M. B. A. Oldstone et al. "Mapping the Anatomy of the Immunodominant Domain of the Human Immunodeficiency Virus gp41 Transmembrane Protein: Peptide Conformation Analysis Using Monoclonal Antibodies and Proton Nuclear Magnetic Resonance Spectroscopy" *J. Virol.* 65, 1727–1734 (1991)].

The transmembrane site (amino acids 684–700) and membrane-associated site (amino acids 525–535) of gp41 were identified by hydrophobicity plotting using a window size of 19 and the algorithm of Kyte/Doolittle [J. Kyte et al. "A Simple Method for Displaying the Hydropathic Character of a Protein" *J. Mol. Biol.* 157, 105–132 (1982)].

The secondary structure of gp120/41 was simulated by the Chou-Fasman method [P. Y. Chou et al. "Empirical Predictions of Protein Conformation" *Ann. Rev. Biochem* 47, 251–276 (1978)], as were α-helices, β-sheets, β-turns, and random coil structures. For determining helical structure, the condition that $P_{(bound)}$ is greater than 1.0 and that $P_\alpha$ is greater than $P_\beta$ was not used. For determining β-sheets, a minimum length of 5 residues is required.

Surface probability and flexibility were also taken into consideration in constructing the model. The computation parameters were used in a default setting, a limit of 5.0 for surface probability, and 1.040 for flexibility. The basic secondary structure was similar in various published HIV-1 sequences [J. Devereux et al. "A Comprehensive Set of Sequence Analysis Programs for the VAX" *Nuc. Acid Res.* 12, 387–395 (1984); E. A. Emini et al. "Induction of Hepatitis A Virus-Neutralizing Antibody by a Virus-Specific Synthetic Peptide" *J. Virol.* 55, 836–839 (1985); P. A. Karplus et al. "Refined Structure of Glutathione Reductase at 1·54 Å Resolution" *J. Mol. Biol.* 195, 701–729 (1987); Modrow et al., "supra"].

Three dimensional model simulation was based on disulfide bond structure and computer calculations of helix, sheet, turn, and random coil structures. The envelope protein gp160 was divided into gp120: amino acids 1–511 and gp41: amino acids 512–856. Four possible motifs were suggested in gp120: amino acids 1–107 (1–29, 33–107), amino acids 108–211, amino acids 213–353, amino acids 358–511. In FIG. 1 the symbols correspond to features as follows:
//—the break between gp120 and gp41 (amino acid 511); ⊂⊃—α-helix; and ⸺—β-pleated sheet.

As can be seen the amino acid sequence of the gp120/41 complex has a number of sites (spanning a total of 152 amino acids) which are similar or identical to a normal protein, 70K (FIG. 1). These similarities, which are shown by shaded bars in FIG. 1 (and are defined more exactly in FIG. 2) include most of the major neutralizing domain of HIV-1, the V3 loop (discussed in detail in FIG. 3, below). 70K is a component of a small nuclear ribonucleoprotein particle (snRNP), whose function is to process (splice) mRNA precursors [M. R. Lerner et al. "Are snRNPs Involved in Splicing?" *Nature* 283, 220–224 (1980); Hamm et al., "In Vitro Assembly of U1 snRNPs" *EMBO J* 6, 3479–3485 (1987)]; D. L. Black et al. "U2 as Well as U1 Small Nuclear Ribonucleoprotein Are Involved In Premessenger RNA Splicing" *Cell* 42, 737–750 (1985)]. The core of the particle is a RNA molecule, U1. Two other proteins, A and C, are specific components of U1 snRNP [Hamm et al., "supra" (1987)]. Other polypeptide components, including B, B', D, E, F and G, are also found in snRNPs having U2–U6 RNAs as their cores [Hamm et al., "supra" (1987)].

The U1 snRNP is the target of high-titer, high avidity autoantibodies occurring in the SRD syndromes: mixed connective tissue disease (MCTD), scleroderma and systemic lupus erythematosus (SLE) [W. N. Kelly et al. "Textbook of Rheumatology" (Saunders, Philadelphia) (1989)]. It is of importance that anti-U1 snRNP antibodies frequently occur in MCTD unmixed with other antibody specificities, and have no known pathologic effects [Kelly et al., "supra"; E. H. Schumacher et al. "Primer on the Rheumatic Diseases" (Arthritis Foundation, Atlanta) 9th Ed. (1988)]. In SLE, where antibody profiles are often mixed, the presence of anti-U1 antibodies is associated with a more favorable prognosis [Kelly et al., "supra"; E. H. Schumacher et al. "Primer on the Rheumatic Diseases" (Arthritis Foundation, Atlanta) 9th Ed. (1988)].

Figure 3:
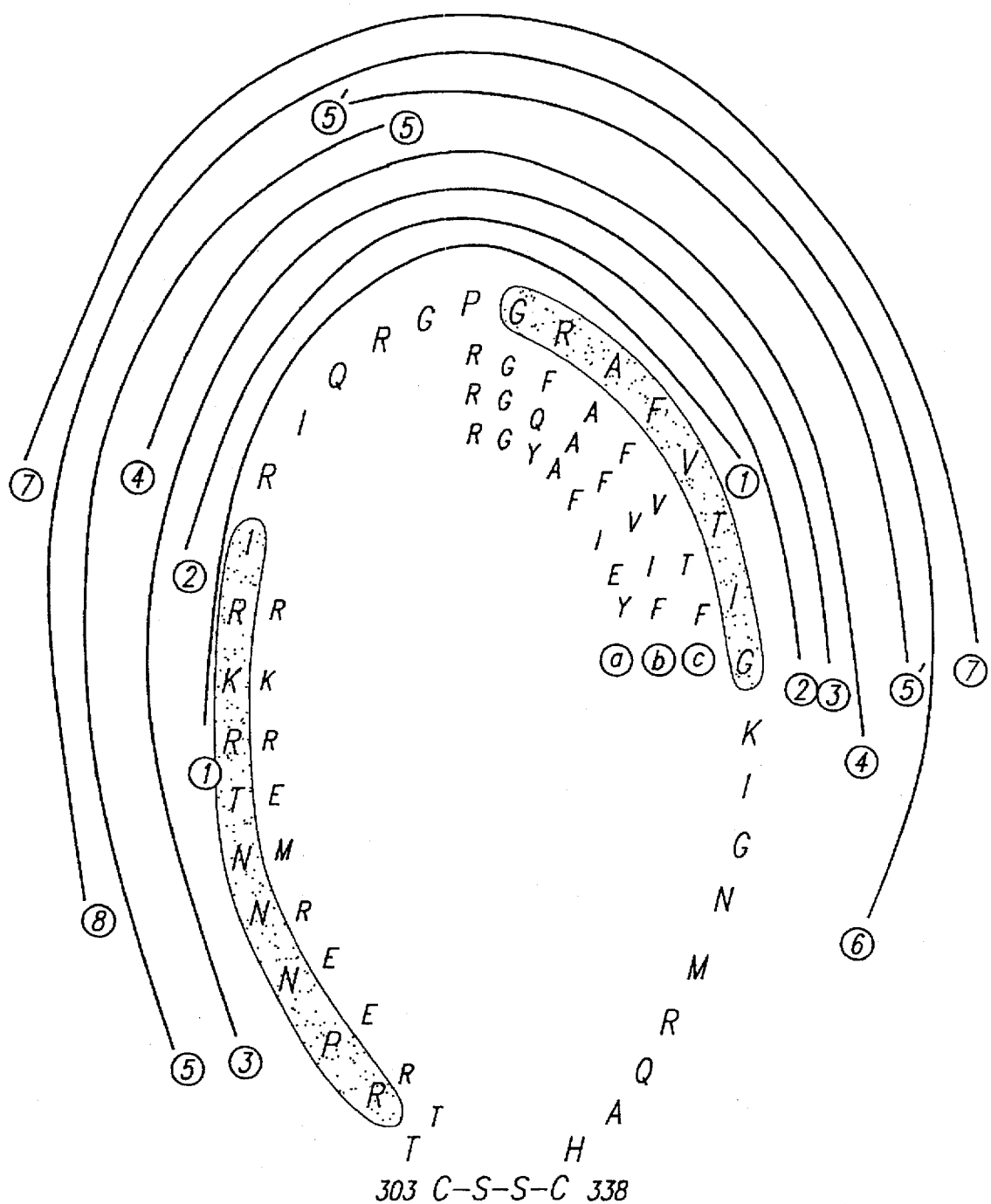
FIG. 3 is an immunological comparison of the $V_3$ loop of gp120 and 70K.

FIGS. 2A–B and 3 illustrate the importance of the consensus binding sequence (cbs) in the proposed strategy of using anti-RNP antibodies to neutralize HIV-1. MCTD is a syndrome which is defined by the presence of serum anti-U1 snRNP antibodies [Kelly et al., "supra"; Schumacher et al., "supra"]. FIG. 2A SEQ ID NOS:20–51 expands the analysis presented in FIG. 1, showing the linear amino acid sequences in 70K (bold type) which are similar to gp120/41. Similarities (with one exception) are defined as sites in which ≧50% of the amino acids are identical. In all, 18 sites in 70K, 26% of its length, are homologous to gp120/41. A key finding is that the 8 amino acid consensus binding sequence (open box at amino acids 322–329) which is necessary and sufficient for high affinity binding to U1 RNA, matches a similar sequence, GRAFVTIG SEQ ID NO:52, in gp120. This site is not an exact sequence but a common sequence found in a family of proteins binding to U1 RNA. As shown in FIG. 2A, the cbs lies in the major epitope domain B of 70K (underlined) which reacts with 100% of MCTD sera [Guldner, et al., "Epitope Mapping with a Recombinant Human 68-kDa (U1) Ribonucleoprotein Antigen Reveals Heterogeneous Autoantibody Profiles in Human Autoimmune Sera" *J. Immunol.* Vol. 141. 469–475 (1988); D. S. Cram et al. "Mapping of Multiple B Cell Epitopes on the 70-Kilodaton Autoantigen of the U1 Ribonucleoprotein Complex" *J. Immunol.* 145, 630–635 (1990)].

The screening of sera for therapeutic use is therefore a matter of identifying those with the highest titers. A second domain, A, also identifies an epitope of importance, reacting with >50% of anti-U1 snRNP sera [Cram et al. "supra"]. As shown in FIG. 2, this epitope also has a homologous sequence in gp120.

FIG. 2B shows the cbs of seven proteins associated with U1 RNA in functional splicing complexes, including 70K SEQ ID NOS:53–59. The 8 amino acids outlined by the solid rectangle are necessary and sufficient for binding to U1 RNA [R. J. Bandziulis et al. "RNA-Binding Proteins as Developmental Regulators" *Genes Devel.* 3, 431–437 (1989); B. M. Merrill et al. "Phenylalanines That Are Conserved Among Several RNA-Binding Proteins Form Part of a Nucleic Acid-Binding Pocket in the A1 Heterogeneous Nuclear Ribonucleoprotein" *J. Biol. Chem* 263, 3307–3313 (1988); B. M. Merrill et al. "Photochemical Cross-Linking of the *Escherichia coli* Single-Stranded DNA-Binding Protein to Oligodeoxynucleotide" *J. Biol. Chem* 259, 10850–10856 (1984); A. Woppman et al. "Direct Cross-Linking of snRNP Protein F and 70K to sn RNAs by Ultra-Violet Radiation In Situ" *Nuc. Acid Res.* 16, 10985–11004 (1988); A. R. Krainer et al. "Functional Expression of Cloned Human Splicing Factor SF2: Homology to RNA-Binding Proteins, U1 70K, and Drosophila Splicing Regulators" *Cell* 66, 383–394 (1991)]. The cbs of hnRNP A2 and B1 are identical. Superimposed on these is the GRAFVTIG SEQ ID NO:60 sequence of V3 (HIV-1 strain III$_B$), with flanking amino acids. The invariant G–F structure occurs in V3 and all seven U1-binding proteins, augmented by the nearly invariant A and V, flanking F. Other conserved sequences within the 8 amino acid cbs also present in the V3 GRAFVTIG SEQ ID NO:60 sequence are apparent. The strategic location of this homolog in the immunodominant V$_3$ loop of gp120 is discussed below.

FIG. 2A also displays extensive homologies between the hydrophilic COOH-end of 70K and gp41. These encompass the repeating RDRDR SEQ ID NO:60 motif, and a block of alternating basic and acidic residues beginning at positions 513 and 732 of 70K and gp41, respectively. In this block, 11 of 18 of the 70K amino acids are identical to gp41, and 3 more represent conservative substitutions of glutamic and aspartic acids. Configurations of alternating basic/acidic amino acids, including RDRDR SEQ ID NO:60, RERRE SEQ ID NO:61 ERKR SEQ ID NO:62 and the consensus sequence ETPEEREERRR SEQ ID NO:63 are antigenic to anti-U1 RNP antibodies [Douvas et al., "supra" (1991); Cram et al., "supra"; C. C. Query et al. "A Common RNA Recognition Motif Identified within a Defined U1 RNA Binding Domain of the 70K U1 snRNP Protein" *Cell* 57, 89–101 (1989)]. Interestingly, the sequence EEEGGE SEQ ID NO:64 in gp41 also occurs in the centromere polypeptide CENP-B, which is the major target of autoantibodies in the scleroderma disorder, one of the clinical components of MCTD. The related sequence EEEGE SEQ ID NO:65, occurring twice in CENP-B, also occurs in the pol protein of HSV-1 [Douvas et al., "supra" (1991)].

Both the cbs and the domain A homolog lie in the V3 loop of gp120, as shown in FIG. 3. FIG. 3 illustrates the importance of the V3 loop in producing antibodies which neutralize the infectivity of the virus. Immunologic analysis of the entire length of gp120/41 by other investigators reveals that the V3 loop is the predominant site of neutralizing epitopes [J. D. Laman et al. "Variant-Specific Monoclonal and Group-Specific Polyclonal Human Immunodeficiency Virus Type 1 Neutralizing Antibodies Raised with Synthetic Peptides from the gp120 Third Variable Domain" *J. Virol.* 66, 1823–1831 (1992)]; Girard et al., "supra"; Broliden et al., "supra"; J. R. Rusche et al. "Antibodies that Inhibit Fusion of Human Immunodeficiency Virus-Infected Cells Bind a 24-Amino Acid Sequence of the Viral Envelope, gp120" *Proc. Natl. Acad. Sci. USA* 85, 2198–2302 (1988); P. J. Durda et al. "HIV-1 Neutralizing Monoclonal Antibodies Induced by a Synthetic Peptide" *AIDS Res. Res. Hum. Retro.* 6, (1990); M. A. Skinner et al. "Characteristics of a Neutralizing Monoclonal Antibody to the HIV Envelope Glycoprotein" *AIDS Res. Hum. Retro.* 4, (1988); K. Javaherian et al. "Principal Neutralizing Domain of the Human Immunodeficiency Virus Type 1 Envelope Protein" *Proc. Natl. Acad. Sci. USA* 86, 6768–6722 (1989)]. Almost all antibodies capable of neutralizing the virus in vitro (or in vivo in primates), react with the V3 loop. This includes antibodies from AIDS patients, generated by monoclonal technology, or produced in monkeys. The V3 loop is therefore the most potent immunogen in the virus.

FIG. 3 SEQ ID NOS:66–70 presents a detailed immunologic analysis of the V3 loop (36 amino acid with a disulfide bond between amino acids 303 and 338), compiled from published studies. Neutralizing domains are represented as solid nested lines around the amino acid sequence. The RKSIRIQRGPGRAFV moiety (line 1) SEQ ID NO:71, overlying parts of both the cbs and domain A epitopes of 70K, is the target of >80% of neutralizing antibodies occurring in HIV-1 infected sera from AIDS patients [Laman, et al., "supra"]. Lines 1–4 delineate the target sequences of anti-gp120 monoclonal antibodies found to be the most potently neutralizing in syncytium formation inhibition assays (SFI) [Laman et al., "supra"; Girard et al., "supra"; Brolinden et al., "supra"; Rusche et al., "supra"]. Use of separate halves of the V3 loop as immunogens, as represented by lines 5 and 5', reveals that the GPGRAFVTIG SEQ ID NO:72 sequence is the more potent inducer of neutralizing monoclonal antibodies [Durda et al., "supra"]. The sequence represented by line 6, when injected into chimpanzees, confers partial protection against challenge with HIV-1 [Skinner et al., "supra"] Further, the sequence IRIQRGPGRAFVTIG (line 7) SEQ ID NO:73 is the dominant epitope of antisera produced in chimpanzees injected with gp120 [Javaherian et al., "supra"].

The superposition of lines 1–7 identifies a roughly 11 amino acid segment of the loop, RGPGRAFVTIG SEQ ID NO:74, which contains the cbs, as the most potent focus of neutralizing antibodies. Moreover, lines 1, 3, 5 and 6, all representing neutralizing epitopes, overly the domain A epitope of 70K. Unfortunately, in AIDS, titers of these antibodies are too low to arrest the disease. However, the homologous sequences in 70K (FIG. 2) are immunodominant targets of autoantibodies in MCTD with titers in some cases exceeding 10$^7$. The remarkable congruence of immunodominant V3 and 70 epitopes strongly predicts that anti-U1 snRNP antibodies will cross-react with the HIV-1 epitopes, and vice versa. The same analysis suggests that the gp41 homologies may also be of importance. These predictions are supported by experimental data presented in FIGS. 4 and 5, below.

FIGS. 4A and B present an experimental analysis, by ELISA, of cross-reactivities between a panel of non-HIV-infected sera and gp120/41 antigens. These are compared to the reactivities of a total of 12 HIV-infected human sera, pre-screened for sero-positivity by western blot analysis. ELISAs were performed by adsorbing saturating concentrations of antigen to plastic microtiter plates (Flow Laboratories) for 12 hrs at 4° C. Recombinant antigens gp120, V3 and gp41 (panels A, B and C, respectively) were purchased from ABT (Cambridge), Sigma (St. Louis) and du Pont (Boston). HIV-1 infected sera (HIV) were pre-screened for seropositivity by western blotting using an Organon Teknika Kit. Sera from MCTD patients having anti-RNP antibodies (RNP) and from Sjogren's patients (SS) were screened for the presence of anti-RNP and anti-Ro/SSA antibodies by using double diffusion assays against standardized cell extracts, using known positive prototype sera for identification of precipitin lines. Thyroiditis sera were obtained from patients having clinical thyroiditis. Th-U and Th-T denote untreated and treated, respectively. Normal sera (NL) were collected from volunteers, and were determined to be negative for anti-nuclear antibodies by immunofluorescence. All sera were diluted 1:100 in phosphate buffered saline (PBS) Ph 7.5, 0.1% bovine serum albumin (BSA). Horse-radish peroxidase conjugated goat anti-human IgG (1:1000 dilution) was employed as a second antibody (Zymed Inc.) and o-phenyldiamine dihydrochloride (Sigma) as a substrate. Optical densities (arbitrary units at O.D. 490 nm) were recorded using an automated ELISA reader. Horizontal bars indicate the mean of each serum group.

Panel A of FIG. 4A compares the reactivities of HIV sera to anti-RNP sera (RNP), normals (NL), and a rheumatoid control group of patients with Sjogren's syndrome (SS) to gp120. The mean reactivities of RNP and SS were 0.137 and 0.143, versus 0.673 and 0.033 for HIV and NL, respectively. The substrate in panel B is the 38 amino acid V3 chain. The highest reactivity in this series was seen in the RNP group (mean of 0.285 versus 0.261 for HIV, 0.160, and 0.099 for SS and NL, respectively). The 2.6-fold lower reactivity of HIV sera to V3 versus gp120 is consistent with the smaller number of different epitopes in V3. However, the >2-fold higher RNP reactivity to V3 versus gp120 is highly significant, given that there are only two homologous sequences in V3 to 70K (a total of 27 amino acids in 70K) versus 6 homologies in the rest of gp120 (a total of 47 non-V3 amino acids in 70K). This pattern is consistent with sequence-specific recognition by anti-RNP antibodies of higher affinity epitopes in V3. It is assumed that the antigen-specific reactivities reported in FIG. 4A are due to antibodies, and not to other serum components. As proof of this assumption, we have repeated some of these experiments using purified IgG from three of the anti-RNP sera, and using horse radish conjugate anti-IgG, rather than anti-Ig in repeating a number of the assays. These experiments yield identical specificities and equivalent affinities as those reported in FIG. 4A. Moreover, heat treatment of sera (56° C., 30 minutes) did not destroy reactivity. SS sera showed no significant difference between gp120 and V3 reactivity.

Figure 4B:
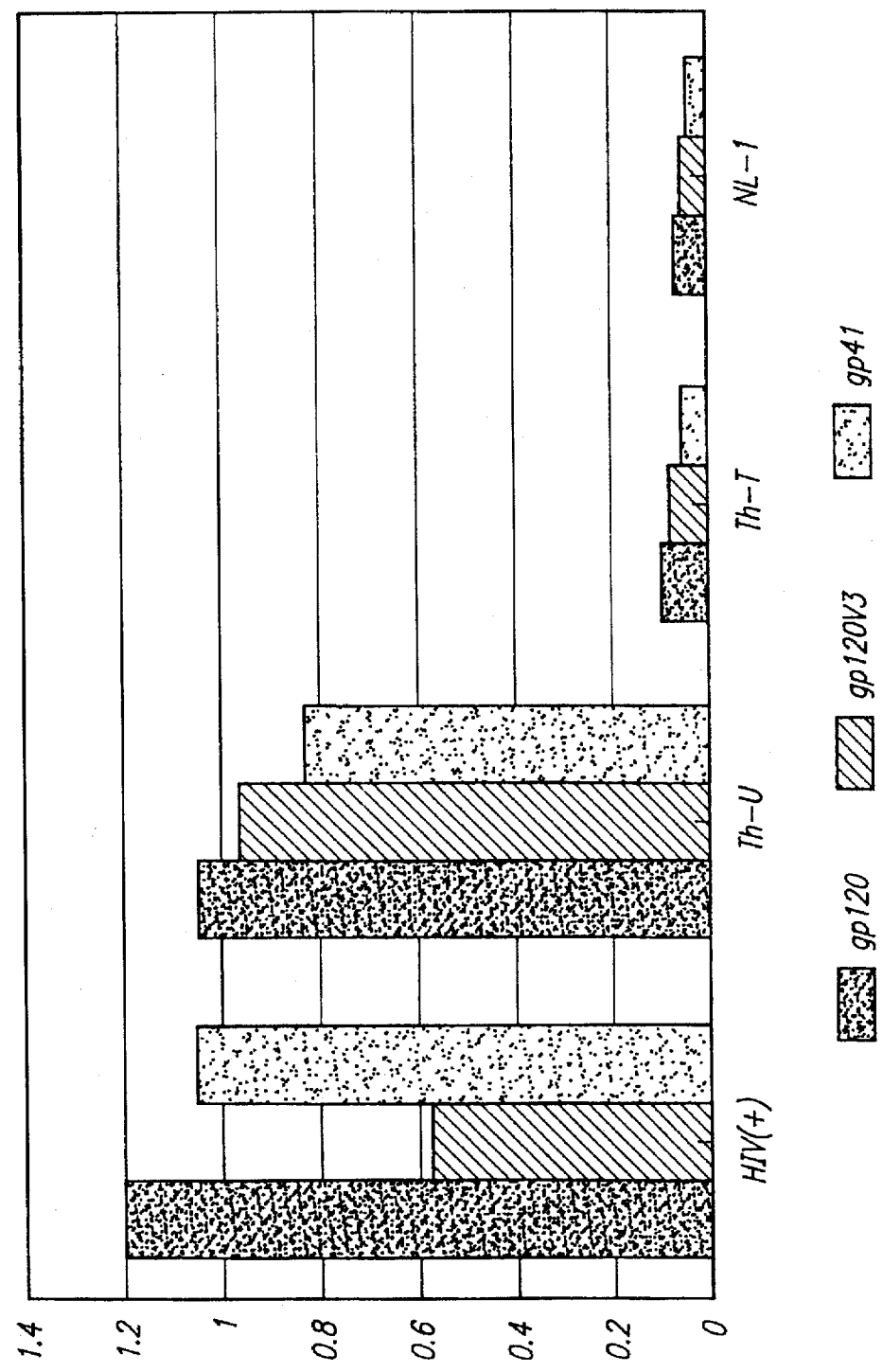
FIG. 4A and B show an experimental analysis, by ELISA, of cross-reactivities between non-HIV-1-infected sera and gp120/41 antigens, in comparison to HIV-infected sera.

As predicted from the hydrophilic homologies in FIG. 2A, gp41 was a better substrate for RNP than gp120 (means of 0.266 versus 0.137), whereas the SS group showed no significant preference (mean reactivities of 0.150 versus 0.143, respectively). However, the equivalent to slightly higher reactivity of RNP sera to V3 versus gp41 is again remarkable, because compared to the two homologies between V3 and 70K there are 11 homologies between gp41 and 70K (93 amino acids in 70K). At least 9 of these homologies are hydrophilic [Douvas et al., "supra" (1991)]. FIG. 4B extends the analysis in FIG. 4A to serum from two thyroiditis patients, one prior to treatment (Th-U) and one after treatment for more than one year (Th-T). A positive control (HIV(+)) and a normal serum are also shown. It is dramatically apparent that the untreated thyroiditis patient serum reacts with HIV gp-120, pg41 and with the V3 loop. This is consistent with the computer-assisted analysis showing hydrophilic sequences similar to those of CENP-B and 70K in both thyroid peroxidase (TPO) and thyroglobulin (see Table I).

Figure 5:
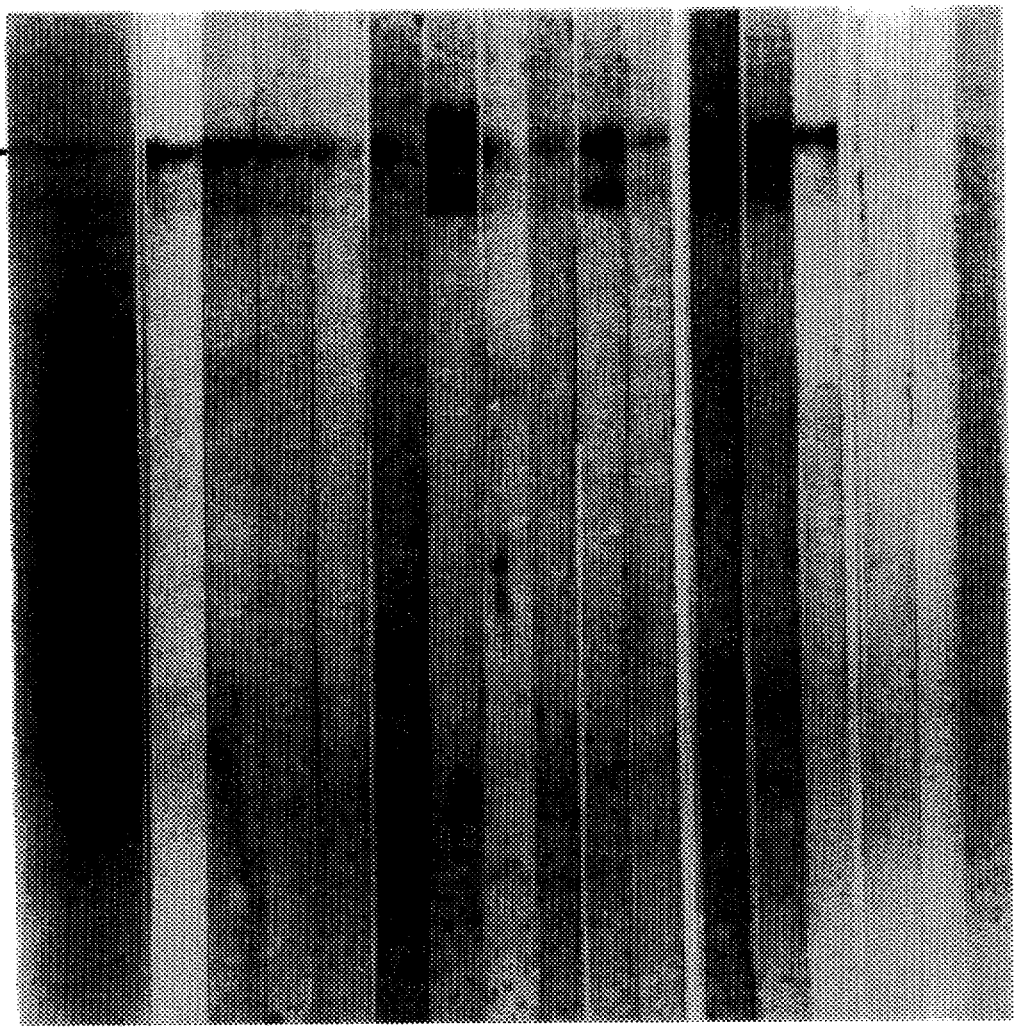
FIG. 5 shows Western blot reactivities of HIV-1 autoimmune and control sera to U1 snRNP 70K.

FIG. 5 demonstrates, by western blotting, that AIDS sera react specifically with the 70K moiety of the RNP antigen. In FIG. 5, partially purified 70K was isolated from rat liver nuclei by differential centrifugation and affinity column chromatography (on anti-RNP IgG-Sepharose), and polyacrylamide gel electrophoresis (10%) and western blotting were performed as described in A. S. Douvas et al. [A. S. Douvas "Autoantibodies Occurring in Two Different Rheumatic Diseases React with the Same Nuclear Ribonucleoprotein Particle" Proc. Natl. Acad. Sci. USA 79, 5401–5405 (1982)] and in M. C. Crow et al. [M. C. Crow et al. "Human Peripheral Blood T Helper Cell-Induced B Cell Activation Results in B Cell Surface Expression of the CD23 (BLAST-2) Antigen" Cell. Immunol. 121, 99–112 (1989)], respectively. HIV-infected, anti-RNP and normal sera were obtained as described previously, and diluted 1:250 for western blotting. Blots were developed using horse radish peroxidase-conjugated goat anti-human IgG (1:3000 dilution) as a second antibody (Tago). In FIG. 5, Lane 1: Polyacrylamide gel of partially purified U1 snRNP 70K antigen, showing 70K and a 60K breakdown product; Lanes 2–11: Western Blot Strips reacted with HIV-1-positive human sera; Lanes 12–14: Western blot strips reacted with anti-RNP sera from MCTD patients; Lane 15: Strip processed as above, but without a first antibody; and Lane 16–18: Western blot strips reacted with control human sera. Of 10 AIDS sera tested, 8 reacted with 70K, with one serum (lane 7) consistently reacting more strongly than 3 anti-U1 RNP sera from MCTD patients (lanes 12–14).

The combination of ELISA and western blot data (FIGS. 4 and 5) thus demonstrate a cross-reactivity between anti-U1 RNP sera and HIV-1 antigens, and between AIDS sera and U1 RNP, and specifically the 70K moiety of U1 RNP. It is not surprising that quantitatively, anti-U1 RNP sera are less reactive against AIDS sera in the HIV-1 ELISAs, since the HIV sera are reacting with non-homologous as well as homologous epitopes. Further, the ELISA is not a measure of the neutralizing capacity of the sera. The neutralizing factor will be measured in pre-screening donor anti-RNP plasma for use in clinical trials.

One concludes from these analyses that structural homologies between gp120/41 and 70K are predominantly the basis for cross-reactivities between anti-RNP antibodies and the end complex. Moreover, the affinity of anti-RNP antibodies for V3 appears to involve sequence-specific recognition of mutual epitopes. The V3 loop is both 50% homologous to 70K, and includes segments of the two immunodominant regions of 70K. The sole hydrophilic segment of V3 cannot be the basis of this affinity, given that (as discussed above) the numerical superiority of hydrophilic homologies in gp41 does not confer an advantage over V3. The GRAFVTIG SEQ ID NO:20 sequence must therefore play an important role in the sequence-specific interaction.

The above analyses also suggest that high-titer anti-RNP antibodies (titers of >$10^7$ are not uncommon) may neutralize HIV-1 infectivity in a manner similar to that of antibodies occurring in infected sera. A question arises, however, as to whether the potential utility of such an interaction would be limited by viral strain specificity.

Table IV demonstrates the neutralization of both HIV-1 strains IIIB and MN by select autoimmune antibody containing sera. The neutralization (viral inhibition) assay employed was a syncytium formation inhibition test. The assay system is described in detail in [P. L. Nara, et al. "Simple, Rapid, Quantitative, Syncytium-Forming Microassay for the Detection of Human Immunodeficiency Virus Neutralizing Antibody" *AIDS Res. Hum. Retro.* 3: 283–302 (1987) (incorporated herein by reference)]. Briefly, the virus-syncytial sensitive cell line CEM-SS is infected with either MN or IIIB strains of HIV-1, and plated in microtiter wells (50,000 cells per well) with or without test serum. Infection results in fusion of individual cells to form large aggregates, or syncytia. The number of syncytial units formed (SFu) are counted under a microscope. The total number formed in the absence of an inhibitory antibody is designated Vo. The number formed in the presence of a test antibody is Vn. Test antibodies are applied at dilutions of 1:8 to 1:64. The ratio Vn/Vo is a measure of the inhibitory potency of the antibody. Total inhibition gives a Vn/Vo score of nearly zero. A Vn/Vo value of 0.5 denotes 50% inhibition, or 50% fewer SFu seen, whereas a value of 1+ denotes no inhibition by the test antibody. It can be seen in Table IV that the anti-RNP serum is a potent inhibitor of both IIIB and MN strains, whereas this anti-centromere serum is only effective against IIIB.

The functional unit, rather than the exact sequence, is the stronger determinant of antibody recognition. Moreover, conserved residues in the principal neutralizing determinant of V3 are congruent with the invariant G-AF—pattern in the cbs. [G. J. LaRosa et al. "Conserved Sequence and Structural Elements in the HIV-1 Principal Neutralizing Determinant" *Science* 249, 932–935 (1990); G. J. LaRosa et al. "Conserved Sequence and Structural Elements in the HIV-1 Principal Neutralizing Determinant: Corrections and Clarifications" *Science* 251, 811 (1991); G. J. LaRosa et al. "Conserved Sequence and Structural Elements in the HIV-1 Principal Neutralizing Determinant: Further Clarifications" *Science* 253, 1146 (1991)]. The data (FIGS. 1 and 2A–B and Example 4) suggest that RNA splicing may be a post-attachment function of the gp120/41 complex. The anti-U1 snRNP antibodies occurring in MCTD patients are potent inhibitors of RNA splicing [M. R. Lerner et al. "Antibodies to Small Nuclear RNAs Complexed with Proteins are Produced by Patients with Systemic Lupus Erythematosus" *Proc. Natl. Acad. Sci. USA* 76, 5495–5499 (1979)]. Additionally, there are a number of pharmacologic inhibitors of splicing, including those which inhibit RNA self-splicing [M. Harbers et al. "Suppression of c-fos Precursor RNA Splicing by the Protein Kinase C Inhibitor H76 [1-(5-isoquinolinesulphonyl)-2-methylpiperazine]" *Biochem J.* 278, 305–308 (1991); U. Von Ahsen et al. "Antibiotic Inhibition of Group I Ribozyme Function" *Nature* 353, 368–370 (1991); H. F. Noller "Drugs and the RNA World" *Nature* 353, 302–303 (1991); S. Piñol-Roma et al. "Shuttling of pre-mRNA Binding Proteins Between Nucleus and Cytoplasm" *Nature* 355, 730–732 (1992)]. Exemplary but not limiting examples of RNA splicing inhibitors useful in the practice of the present invention are H7[1-(5-isoquinolinesulphonyl)-2-methylpiperazone], 2-aminopurine and aminoglycoside antibiotics, which include but are not limited to gentamicin, kanamycin and neomicin.

U1 Binding to gp120/41 of HIV-1

Figure 8A:
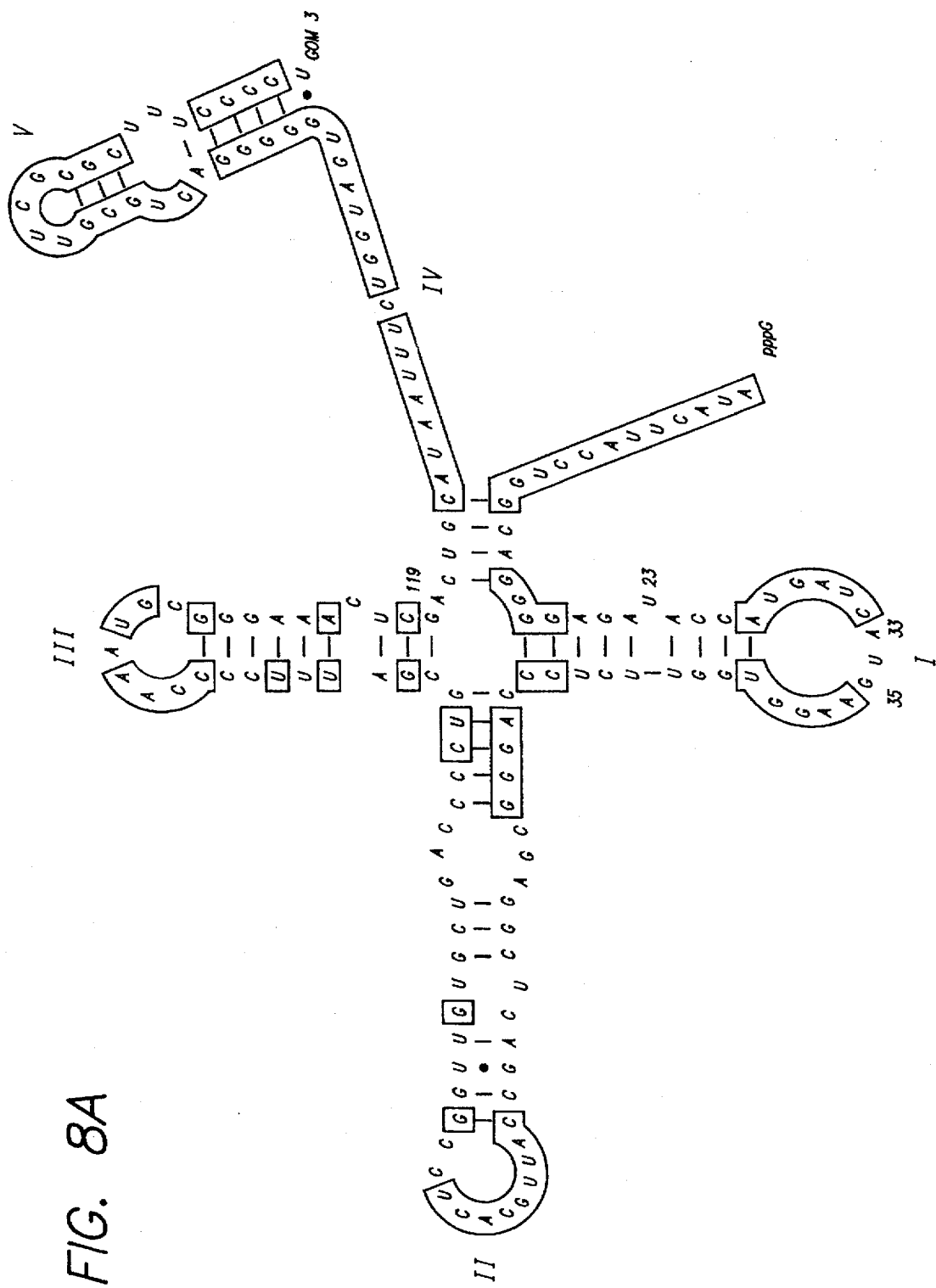
FIG. 8A and B show a model of the U1 RNA and stem-loop I.

The RNA moiety of antigenic RNP particles, U1, may be bound to gp120/41 by in vivo infusion of U1. This strategy, as developed in Examples 3 and 4, has a dual purpose. First, it should increase the avidity of anti-RNP antibodies for gp120/41, based on avidity studies with nuclear RNP antigen [A. S. Douvas et al. "Isolation and Characterization of Nuclear Ribonucleoprotein Complexes Using Human Anti-Nuclear Ribonucleoprotein Antibodies" *J. Biol. Chem.* 254, 3608–3616 (1979) (incorporated herein by reference)]. Second, using UV light, it should be possible to irreversibly cross-link the U1 to the V3 loop of gp120. This treatment should not only destroy the functional capacity of the V3 loop, but as discussed below, should also occlude the CD4 binding site in the adjacent V4 loop. The feasibility of this approach rests on several known properties of U1-cbs interactions. The entire U1 molecule is shown in FIG. 8A SEQ ID NO:75 from Hamm et al., [J. Hamm et al. "Loop I of U1 Small Nuclear RNA is the Only Essential RNA Sequence for Binding of Specific U1 Small Nuclear Ribonucleoprotein Particle Proteins" *Mol. Cell Biol.* 8, 4187–4791 (1988)]. The cbs of U1-binding molecules (shown in FIGS. 2A–B) reacts with a specific part of the U1 molecule, stem-loop I, shown in FIG. 8B.

Binding and cross-linking of U1 RNA, and derivatives to the V3 region of gp120/41, is anticipated to overlie and occlude the CD4 binding site in V4. This prediction is based on the relative sizes of U1 and gp120. The U1 snRNP is estimated by electron microscopy to have dimensions of 11–15 nm (length) by 11–12 nm (width) [B. Kastner et al. "Electron Microscopy of U1 Small Nuclear Ribonucleoprotein Particles: Shape of the Particle and Position of the 5' RNA Terminus" *EMBO J.* 8, 227–286 (1989)]. Assuming only one-half of these dimensions are due to the RNA skeleton, a diameter of approximately 6 nm is estimated for U1, as compared to 8–10 nm for the entire globular gp120 [D. J. Thomas et al. "gp160, the Envelope Glycoprotein of Human Immunodeficiency Virus Type 1, Is a Dimer of 125-Kilodalton Subunits Stabilized Through Interactions Between Their gp41 Domains" *J. Virol.* 65, 3797–3803 (1991)]. Thus, on the basis of the foregoing data one may predict that U1 will span the considerably shorter distance between V3 and V4 (see FIG. 1);

Similarly, anti-RNP antibodies bound to $V_3$ are likely to obscure the CD4 binding site. The distance between antigen-binding sites in bivalent IgG is 14–15 nm. Further, although anti-RNP antibodies are predicted to bind to gp120/41 alone (FIGS. 4 and 5), when an RNA moiety is present, the antibodies may not only bind, but also cross-link multiple complexes. Thus the complex of U1-gp120/41 is likely to be more effectively neutralized in vivo than gp120/41 alone.

In addition to its negative effects on the attachment and fusion role of gp120/41, covalent attachment of U1 is likely to neutralize any post-attachment functions of gp120/41. Although a post-attachment function for gp120/41 is strongly suggested by in vitro studies [Habeshaw et al. "supra"], its exact role has not, thus far, been elucidated. The data herein presented suggests that this function involves RNA splicing, which is as vital to viral propagation as it is to the host cell. Thus RNA splicing inhibitors may be used as anti-viral agents.

Therapeutic Strategies for Treating HIV-1 Infections

There are five basic strategies, which may be used alone or in combination for treating HIV-1 infection in human subjects. First, immunotherapies can be used involving autoimmune human anti-RNP antibodies, human autoantibodies of other specificities (e.g. anti-centromere) or of mixed specificities, or technologically derived antibodies which target RNP-homologous epitopes or RNP-related mechanisms and functions (e.g. splicing). Second, therapies involving the use of U1 RNA, fragments thereof, or analogs designed to mimic or improve on interactions between U1 and proteins can be used. Third, therapies involving the use of combinations of anti-RNP antibodies and RNA moieties aimed at occluding, cross-linking and otherwise abolishing the attachment and fusion of gp120/41 to host structures can be used to reduce viral infectivity. Fourth, therapies involving the use of UV light, delivered by photophoresis, laser sources, etc., or other cross-linking strategies can be aimed at stabilizing complexes between antibodies and/or RNA analogs and the virus. Fifth, therapies involving use of pharmacologic inhibitors of RNA splicing to interfere with viral function can be used.

Immunotherapies—In addition to the use of SRD autoantibodies (which will be obtained from screened donors by plasmaphoresis), it is possible to generate either synthetic or murine monoclonal antibodies to RNP epitopes (using native immunogens or immunogenic peptides developed as fusion proteins) [C. S. Surowy et al. "Direct, Sequence-Specific Binding of the Human U1-70K Ribonucleoprotein Antigen Protein to Loop I of U1 Small Nuclear RNA" *Mol. Cell. Biol.* 9, 4179–4186 (1989); Query et al., "supra" (1989); C. C. Query et al. "A Specific 31-Nucleotide Domain of U1 RNA Directly Interacts with the 70K Small Nuclear Ribonucleoprotein Component" *Mol. Cell Biol.* 9, 4872–4881 (1989); Reuter et al., "supra" (1986); (all of which are incorporated herein by reference)]. Several useful modifications of the murine monoclonal antibody approach can be implemented with the goals of maximally impairing viral infectivity, increasing the specificity of therapeutic interactions, and reducing anaphylaxis and other complication arising from introducing non-autologous antibodies.

These modifications include the use of catalytic antibodies. Their potential uses include, but are not limited to the following: catalyzing covalent (irreversible) bond formation to the V3 loop; ligation of polynucleotides, especially U1, to V3 for the purpose of enhancing its recognition by antibodies or impairing its functions; hydrolysis of the V3 loop or other parts of the gp120/41 complex; introduction of electrophilic groups which will maximally react with hydrophilic epitopes; and delivery of splicing inhibitors [K. M. Shoat et al. "Catalytic Antibodies" *Methods Enzymol.* 203, 327–351 (1991); D. Hilvert et al. "Antibody Catalysis of Concerted, Carbon—Carbon Bond-Forming Reactions" *Methods Enzymol.* 203, 352–369 (1991); S. K. Dower et al. "Phosphorus—31 Nuclear Magnetic Resonance Probes for the Combining Site of the Myeloma Protein M315" *Biochem* 18, 3668–3674 (1979); K. D. Janda et al. "Bait and Switch Strategy for Obtaining Catalytic Antibodies with Acyl-Transfer Capabilities" *J. Am. Chem.* Soc. 112, 1274–1277 (1990) (all incorporated herein by reference)]. Catalytic groups can be introduced into the antibodies by established procedures including selective chemical modification, site-directed mutagenesis or genetic selection or screening [Shoat et al., "supra"; Hilvert et al., "supra" (both incorporated herein by reference)].

Another useful modification involves the use of high affinity Fv fragments and sFv. Heterodimers of only the variable region of antibodies ($V_H$–$V_L$) can be produced by recombinant and monoclonal technology to minimize human reactions to murine isotypes [J. S. Huston et al. "Protein Engineering of Antibody Binding Sites: Recovery of Specific Activity in an Anti-Digoxin Single-Chain Fv Analogue Produced in *Escherichia coli*" *Proc. Natl. Acad. Sci. USA* 85, 5879–5883 (1988); M. S. Tai et al. "A Bifunctional Fusion Protein Containing Fc-Binding Fragment B of Staphyloccocal Protein A Amino Terminal to Antidigoxin Single-Chain Fv" *Biochem* 29, 8024–8030 (1990)]. The fragments (Fv) have the advantage of improved biodistribution kinetics [J. S. Huston et al. "Protein Engineering of Single-Chain Fv Analogs and Fusion Proteins" *Methods Enzymol.* 203, 46–88 (1991)]. Light and variable regions can also be produced as a single chain, sFv, and expressed in bacterial vectors [S. Johnson et al. "Construction of single-Chain Fv Derivatives of Monoclonal Antibodies and Their Production in *Escherichia coli*" *Methods Enzymol.* 203, 88–98 (1991)]. In addition to the potential for engineering high-affinity antigen-combining sites, this technology allows for combining the sFv to other effector functions [R. Glockshuber et al. "A Comparison of Strategies To Stabilize Immunoglobulin Fv-Fragments" *Biochem.* 29, 1362–1367 (1990)].

Another useful modification involves the replacement of murine with human isotypes. To minimize allergic reactions to murine isotypes it is possible to produce chimeric antibodies [D. Güssow et al. "Humanization of Monoclonal Antibodies" *Method Enzymol* 203, 99–120 (1991)], or to insert murine complementarity determining regions (CDRs) into human framework sequences [P. T. Jones et al. "Replacing the Complementarity-Determining Regions in a Human Antibody with Those From a Mouse" *Nature* 321, 522–525 (1986); L. Riechmann et al. "Reshaping Human Antibodies For Therapy" *Nature* 332, 323–327 (1988)]. However, allergic reactions may not materialize as a serious problem in treating patients with HIV-1 infections because of their reduced ability to respond to specific antigens.

Yet another useful modification involves the use of antibodies with ligands for covalent attachment to surface gp120/41. Covalent ligands (including photoactivated cross-linkers) can be incorporated using established techniques including chemical modifications or genetic methods as discussed above. Photochemical cross-linking can then be performed in vivo using UV light as discussed below.

U1 RNA, fragments thereof and analogs—Using recombinant U1 DNA flanked at the 5'-end by either T7 or SP6 RNA polymerase promoters, and at the 3'-end by restriction endonuclease sites it is possible to generate gram quantities of U1 for therapeutic use [Merrill et al., "supra" (1988); Hamm et al., "supra" (1988); Surowy et al., "supra"; Query et al., "supra" (1989); Query et al., "supra" (1989); J. R. Patton et al. "Reconstitution of the U1 Small Nuclear Ribonucleoprotein Particle" *Mol. Cell. Biol.* 7, 4030–4037 (1987); C. Lutz-Freyermuth et al. "Quantitative Determination that One of Two Potential RNA-Binding Domains of the A Protein Component of the U1 Small Nuclear Ribonucleoprotein Complex Binds with High Affinity to Stem-Loop II of U1 RNA" *Proc. Natl. Acad. Sci. USA* 87, 6393–6397 (1990); W. Boelens et al. "Analysis of In Vitro Binding of U1-A Protein Mutants to U1 snRNA" *Nuc. Acid Res.* 19, 4611–4618 (1991)].

Further, by selective use of restriction enzymes and/or site directed mutagenesis, it is possible to eliminate undesired regions of the molecule [Merrill et al., "supra" (1984); Hamm et al., "supra" (1988); Surowy et al., "supra"; Query et al., "supra" (1989); Query et al., "supra" (1989); Patton et al., "supra"; Lutz-Freyermuth et al., "supra"].

The high affinity of loop I of U1 for the cbs present in the V3 loop makes binding in the circulation likely. In addition, as described hereinabove, this affinity, due in part to phenylalanine groups in the cbs, promotes rapid and specific cross-linking between the cbs and loop I (see Example 4). Cross-linking can be achieved by established techniques which include introduction of reactive chemical groups into the RNA ligands during synthesis and/or using UV light.

Combination of antibodies and RNA—The advantages offered by using both anti-RNP antibodies and RNA were discussed hereinabove. These relate to the high avidity of human anti-RNP antibodies for the complex of RNA and proteins, and the increased likelihood of cross-linking and of forming large agglomerates of inactivated viral surface groups. Further, three cross-linking targets are provided by this strategy: antibody to RNA, RNA to gp120/41, and antibody to gp120/41.

UV crosslinking—Irreversible inactivation of infective viral surface groups can be achieved by irreversible cross-linking the above-mentioned targets. In addition to chemical cross-linking, this can be achieved using a conventional source of UV light, at relatively low levels of 254 nm irradiation (see Example 4) [Merrill et al., "supra" (1988); Merrill et al., "supra" (1984); Woppman et al., "supra"].

It is possible to deliver sufficient radiation to humans by photophoresis, a treatment modality approved for lymphomas, and which has been used for the treatment of scleroderma patients. The conventional modality uses the drug methoxsalen as a cross-linking agent. Other possibilities involve the use of monochromatic UV light from a laser source [J. W. Hockensmith et al. "Laser Cross-Linking of Nucleic Acids to Proteins" *J. Biol. Chem.* 261, 3512–3518 (1986)]. UV irradiation of blood (into which therapeutic agents have been infused) is extracorporeal. Common side effects for photophoresis have been established.

RNA splicing inhibitors—Possible splicing functions associated with the gp120/41 complex have been addressed hereinabove. The binding of U1 RNA to gp160/120/41 in vitro suggests that such an interaction may occur intracellularly between the virus and host cell RNA. Adverse effects on host cell splicing mechanisms from such an interaction may be abrogated by use of splicing inhibitors. Strategies for optimizing delivery of these agents, and their interaction with viral components, are similar to those discussed above, and include the use of antibodies as delivery systems, and cross-linking to render interactions irreversible.

Therapeutic Strategies for Treatment of ICV Infections

Preparation of immunogens from native antigens—Native antigens, including U1 snRNP and CENP-B, can be isolated from mammalian tissues as described by A. S. Douvas et al. [A. S. Douvas et al. "Isolation and Characterization of Nuclear Ribonucleoprotein Complexes Using Human Anti-Nuclear Ribonucleoprotein Antibodies" *J. Biol. Chem.* 254, 3608–3616 (1979)]; and Earnshaw et al. "supra". To isolate hydrophilic domains of individual antigens, including the acidic domains of CENP-B and the alternating RDRDRDR domain of 70K [H. Theissen et al. "Cloning of the Human cDNA for the U1 RNA-Associated 70K Protein" *EMBO J.* 5, 3209,3217 (1986)], the strategy of generating the corresponding cDNAs by polymerase chain reaction (PCR), followed by their insertion into the over-expression vector pDIP19 for expression in *E. coli* may be employed [B. Singer et al. "Phage T4 Expression Vector: Protection From Proteolysis" *Gene* 106, 1–6 (1991)]. CENP-B domain 1 thus prepared reacts with anti-centromere antibodies by ELISA.

Antibodies for immunotherapy—As in the case of specific immunotherapy for HIV-1 infection (above), SRD autoantibodies reacting with epitopes homologous to HIV-1, HSV-1, CMV, EB-V and other relevant synergizing viruses may be obtained by plasmaphoresis, and used individually or as mixtures. Monoclonal and technologically engineered antibodies may be prepared using native and recombinant antigens as described in the above. Modifications which will be of particular importance for interacting with hydrophilic epitopes include introduction of electrophilic groups into antigen-combining sites.

The invention may be better understood with reference to the accompanying examples, which are intended to be illustrative only and should not be viewed as in any sense limiting the scope of the invention, which is defined hereinafter in the accompanying claims.

EXAMPLES

Example 1

ELISA Comparisons of Cross-Reactivities of Anti-Centromere and Control Sera to Poly-Aspartic Acid, Poly-Glutamic Acid and Poly-Arginine.

Homologies to HIV-1, HSV-1 and CMV are clustered in two extremely hydrophilic domains of CENP-B and in hydrophilic sequences in 70K and Scl-70. The prediction that autoantibodies reacting with these hydrophilic domains would cross-react with similar hydrophilic sequences occurring in other polypeptides is supported by ELISA data presented in FIG. 7A. In FIG. 7A, anti-centromere sera from patients with scleroderma (CN-1, 2 and 3) were pre-screened for seropositivity by indirect immunofluorescence as described previously [A. S. Douvas et al. "Isolation and Characterization of Nuclear Ribonucleoprotein Complexes Using Human Anti-Nuclear Ribonucleoprotein Antibodies" *J. Biol. Chem.* 254, 3608–3616 (1979)]. Normal sera (NL 1 and 2) were anti-nuclear antibody negative. All sera were diluted by a factor of 1:1000. Polyamino acids (Sigma) were dissolved to 1 µg/µl concentrations in 10 mM Tris-HCl buffer, 0.15M NaCl, pH 7.4. ELISAs were performed as described, hereinabove, with respect to Example 1. The symbols P-Asp, P-Glu, P-Arg and P-Lys denote the polyamino acid substrates aspartic acid, glutamic acid, arginine, and lysine, respectively. All three anti-centromere sera and both anti-Scl-70 sera had higher reactivities to poly-Glu, poly-Asp and poly-Lys than the two normal controls, although one control also reacted substantially with poly-Arg. This result is as predicted, given the diverse reactivities to hydrophilic antigens occurring in the spectrum of SRD autoantibodies. FIG. 7B shows reactivities of four anti-U1 snRNP sera (RNP-1 to 4) to P-Asp, P-Glu, P-Arg and P-Lys. Although the reactivities of the RNP sera to all four substrates are higher than the control, these sera show a preference for arginine as compared to the anti-centromere and anti-Scl-70 sera of FIG. 7A. This is appropriate, given the preponderance of arginine in hydrophilic motifs in 70K (see Tables II and III). The diversity of reactivities shown in FIGS. 7A and B is an advantage in the proposed therapies given that viral hydrophilic epitopes may be purely acidic or of mixed acidity and basicity [A. Douvas et al. "Multiple Overlapping Homologies Between Two Rheumatoid Antigens and Immunosuppressive Viruses" *Proc. Natl. Acad. Sci. USA* 88, 6328–6332 (1991)]. Therefore SRD sera may be screened for the desired spectrum of reactivities. An appropriate mixture can then be selected to target the epitopes of interest. This approach should be effective not only in combating individual viral infections, but also in combating synergizing multiple viruses.

Example 2

ELISA Comparisons of Cross-Reactivities of anti-RNP and Control Sera Against HSV-1 Infected Cells.

Figure 6:
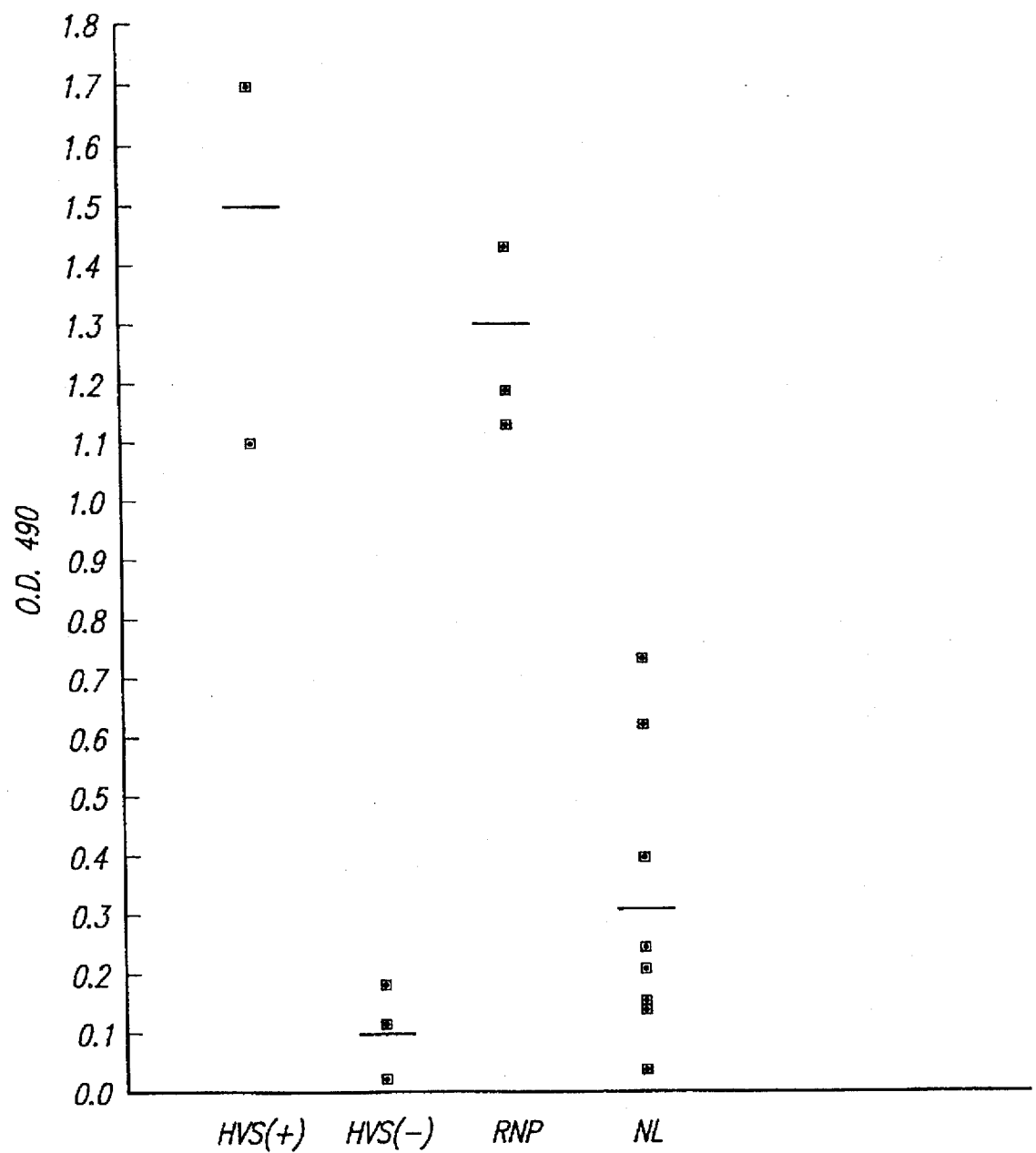
FIG. 6 shows ELISA reactivities of anti-RNP and control sera against HSV-1 infected cells.

Given that regions of sequence homology exist between native antigens and HSV-1, sera containing anti-RNP antibodies were tested for their ability to cross-react with HSV-1 infected cells, and compared in their reactivities to sera pre-selected for high and low reactivity to HSV-1 (HSV(+)

and HSV (−), respectively). Sera designated as NL were from unselected laboratory personnel. FIG. 6 shows a high degree of cross-reactivity between anti-U1 RNP sera and HSV-1 antigens when assayed against extracts of infected Vero cells by ELISA. All sera were diluted 1:1000 in phosphate buffered saline (PBS) pH 7.5 0.1% bovine serum albumin (BSA). ELISAs were performed according to the method of M. K. Crow et al. [M. K. Crow et al. "supra" using horse radish peroxidase—conjugated goat anti-human IgG (1:3000 dilution) as a second antibody (Tago) and O-phenyldiamide dihydrochloride (Sigma) as a substrate. Optical densities were read at 490 nm using an automated ELISA reader. Similar high reactivities were not seen against uninfected Vero cell extracts. This is evidence that viruses with homologies to epitopes in nuclear autoantigens cross-react with the corresponding autoantibodies.

Example 3

U1 RNA and Stem-Loop I.

Figure 8B:
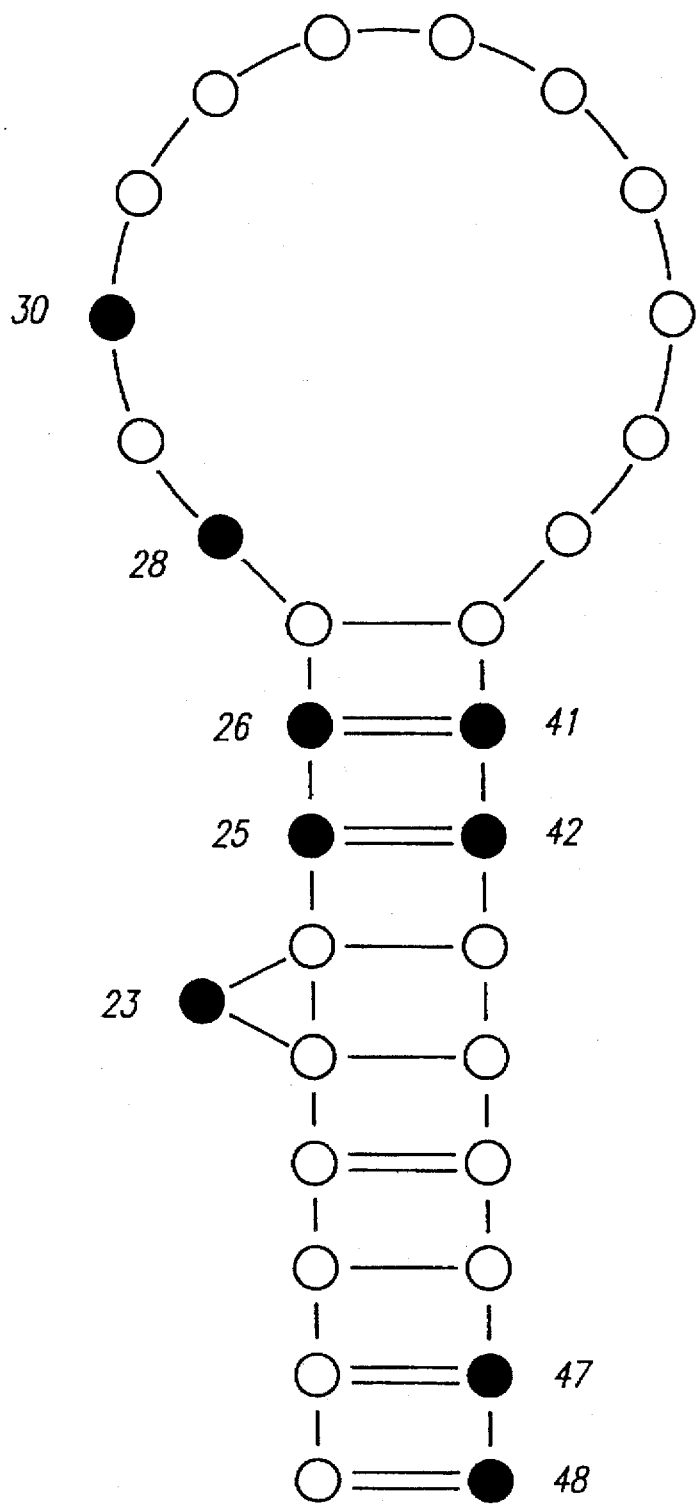

FIG. 8A shows the complete U1 molecule and FIG. 8B shows the stem-Loop I region of U1. Numbers denote nucleotide positions of mutations used to evaluate 70K binding affinity. The binding is sequence-specific, and requires fewer than 15 bases in the loop itself. This property is the basis of the proposal to use fragments of U1 as well as the intact molecule as therapeutic agents. The affinity of this interaction is so high that it is possible to cross-link the cbs to this apex very specifically, using low energy levels of UV light [Merrill et al., "supra" (1988); Merrill et al., "supra" (1984); Woppman et al., "supra" (all of which are incorporated herein by reference)].

Example 4

The Binding of gp160 and gp120/41 to U1 snRNA Transcripts.

Figure 9:
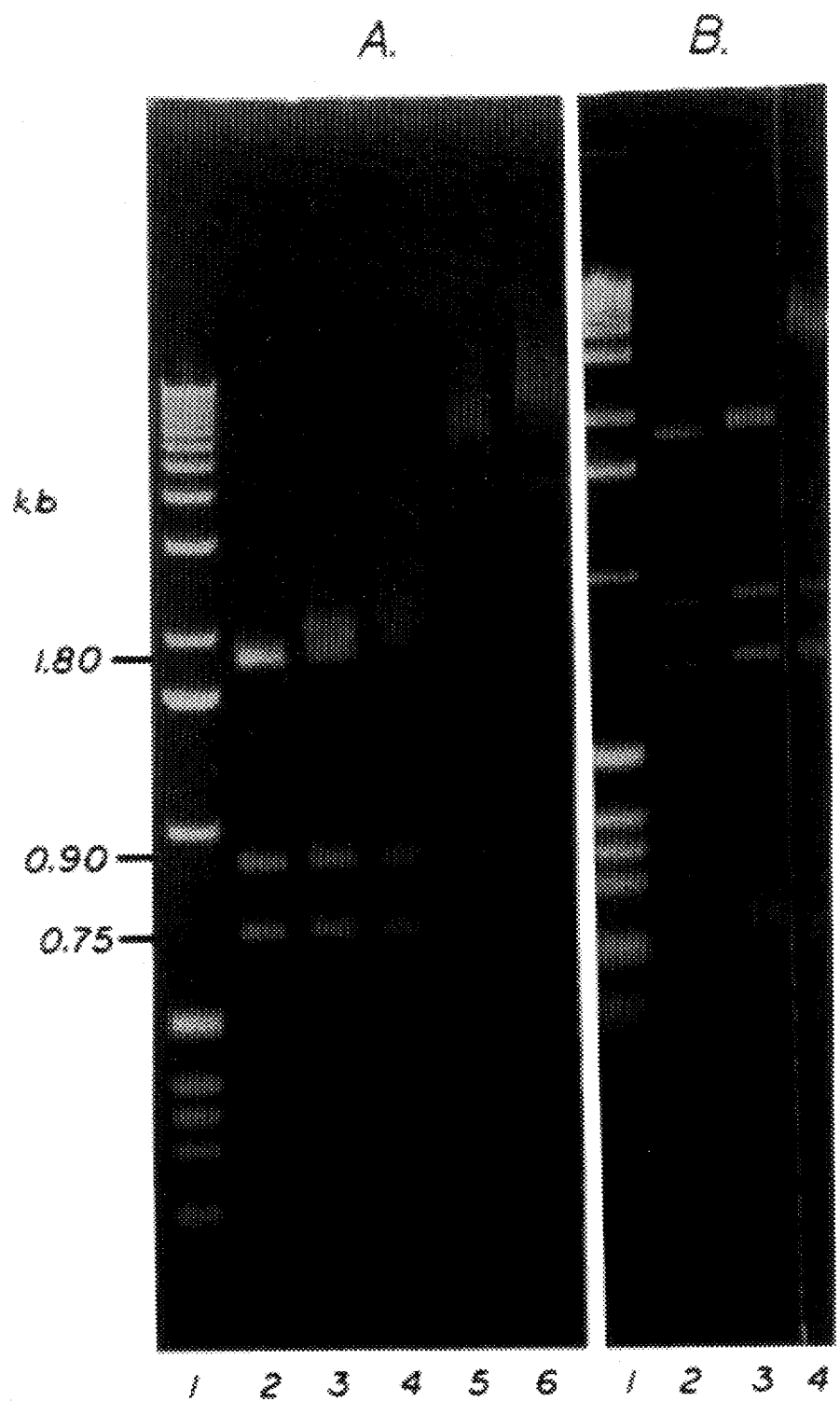
FIG. 9 shows the binding of gp160 and gp120/41 to U1 snRNA transcripts.

Given that gp120 has a cbs, a series of binding experiments were conducted with gp120/41 and U1, with and without UV cross-linking, using agarose gel electrophoresis to separate tightly associated complexes from unreacted U1 (FIG. 9).

FIG. 9 shows the recombinant plasmid pGEM-3Zf(+) (Promega), containing a T7 promoter and U1 DNA, which was cut with restriction endonuclease RsaI, then transcribed as described by J. V. Maizel et al. [J. V. Maizel et al. "Enhanced Graphic Matrix Analysis of Nucleic Acid and Protein Sequences" *Proc. Natl. Acad. Sci. USA* 78, 7665–7669 (1981)], yielding three RNA transcripts of 1.8 kilobases (kb), 0.9 kb and 0.75 kb. Analysis of the substrate fragments reveals that only the larger, yielding the 1.8 kb transcript, contains U1 sequences. Highly purified gp160, partially hydrolyzed into gp120/41 was obtain from a commercial supplier. Approximately 1 µg of RNA transcript was mixed with 3 µl of gp160/120/41 in a total volume of 30 µl TE buffer pH8.0 (Tris-EDTA, as described in ref. 53), and incubated for 12 minutes at 37° C. Samples to be irradiated were placed in molded Para-film, then subjected to 20 mJ/mm² of UV light (254 nm) on ice using a Stratalinker 1800 UV cross-linker (Stratagene, Calif.). Agarose gel electrophoresis (1.5%) was performed as described by J. Shamrock et al. [J. Shambrook et al. "Molecular Cloning" (Cold Spring Harbor Laboratory Press 2nd Ed. (1989)].

Panel A of FIG. 9 shows the titration of RNA transcripts with gp160/120/41 without irradiation. Lane 1: 1 kb DNA ladder markers; lane 2: 1.8, 0.9 and 0.75 kb RNA transcripts; lanes 3–6: the same three transcripts as lane 2 incubated with 0.5, 1.0, 2.5 and 3.5 µl of gp160/120/41, respectively.

Figure 10:
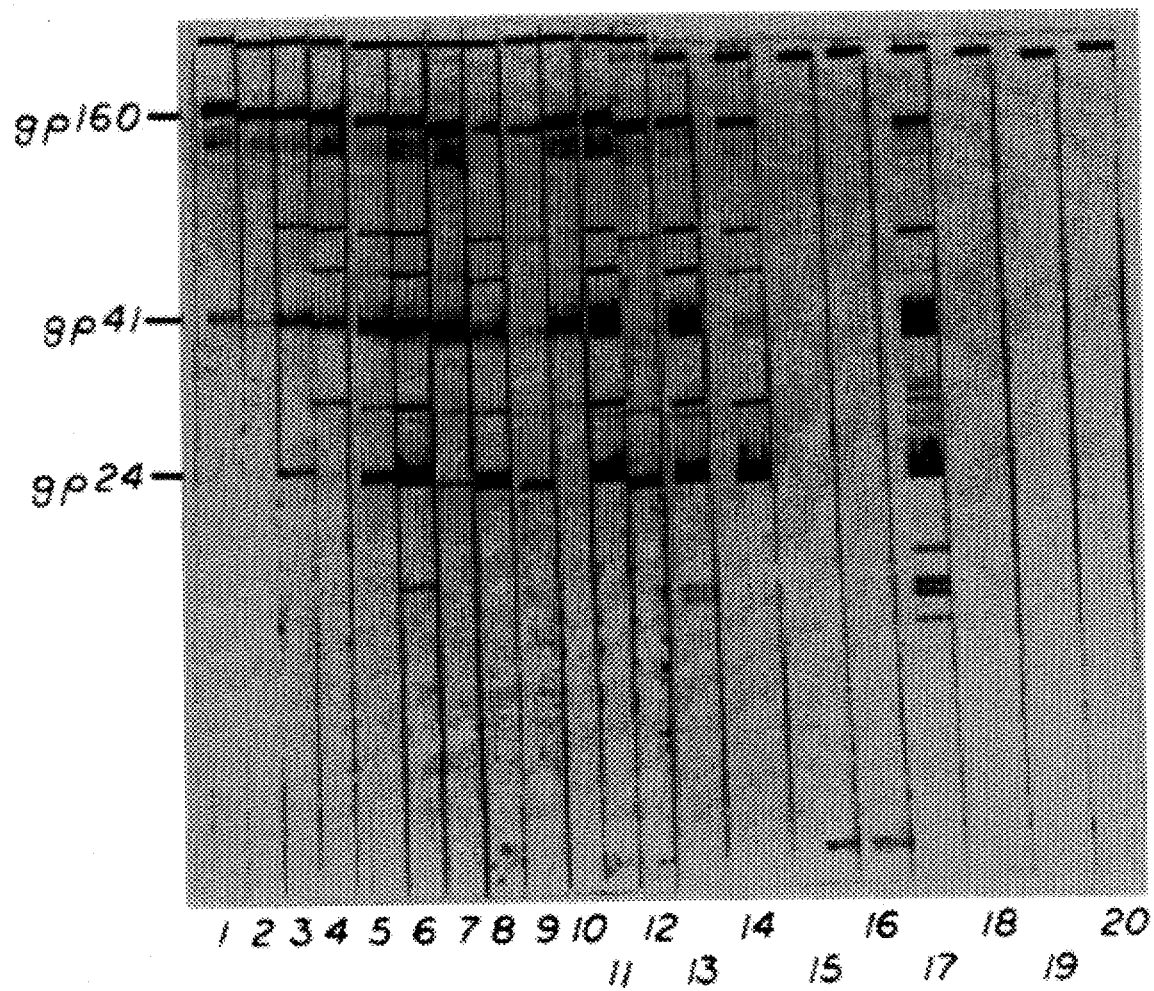
FIG. 10 illustrates, by Western blot, the development of HIV antibodies in an HIV-1 infected patient with high titers of anti-RNP antibodies who is AIDS-free.

Panel B of FIG. 10 shows UV irradiation of mixtures of RNA and gp160/120/41. Lane 1: kb markers; lanes 2 and 3: unirradiated and irradiated RNA transcripts, respectively; lane 4: transcript mixture incubated with 3.5 µl gp160/120/41, then irradiated as above.

U1 which has formed complexes with gp120/41 will migrate slower, and thus appear closer to the top of the gel. FIG. 9A, lane 2 shows three RNA transcripts of a recombinant vector, only the largest of which (1.8 kb) contains U1. Titration of this preparation with the gp120/41 precursor gp160 resulted in a major shift in the mobility of this transcript (lanes 3–6), but not in the 0.90 and 0.75 kb transcripts. The specificity of the interaction is further illustrated in FIG. 9B, in which UV light was used to covalently cross-link complexes. A comparison of lanes 2 and 3 (without and with UV, respectively) shows that UV light alone does not cross link and therefore affect the mobility of the transcripts. Lane 4 shows the effects of adding gp160 and irradiating with UV light. As in lanes 5 and 6 of panel A, the larger transcript (and only this transcript) forms a covalent complex with gp160. The demonstration that gp160 forms complexes with U1 RNA sequences in vitro, with and without UV light, forms the basis of the strategy to use this approach in vivo.

Example 5

AIDS Resistance in HIV-1 Infected Patient with High Titers of anti-RNP Antibodies.

Further support of the utility of anti-RNP antibodies in treating immunoinfective cluster viruses is provided by the following evaluation of an individual (hereinafter, "Mr. M") with a diagnosis of scleroderma, high titers of circulating anti-RNP antibodies, and exposure to seroconversion to HIV(+) status circa 1986.

In 1982, a blood bank specimen dated Sep. 10, 1981 was obtained from Mr. M for evaluation for anti-RNP antibodies (data presented below). He was subsequently followed very infrequently, and was revealed to be HIV-1 exposed. The presentation of his clinical case (immediately below) is followed by a discussion of his HIV disease in relation to the chronology of his exposure.

(1) Clinical Case

Mr. M is a 41 year old caucasian male, with a gay lifestyle. Mr. M was diagnosed at age 12 as having simultaneous onset of JRA (juvenile rheumatoid arthritis) and scleroderma. He was treated with high doses of ASA (aspirin) at the Mayo Clinic. The JRA apparently ceased to be active at age 16, but sclerodermatous changes, particularly in the hands; continue as part of his current clinical course.

In September, 1981, a serum sample was collected. The sample was analyzed in August, 1982 and found to contain a high titer of anti-RNP antibodies. Mr. M came in contact with HIV approximately in 1986. A notation in his chart in July 1986 notes the condition of diffuse adenopathy and indicates that a HIV test is recommended. The patient reports that he was tested for HIV in June 1987 and found to be positive. The test was repeated a year later, and he was confirmed HIV(+).

PAST MEDICAL HISTORY: Mumps, measles, chicken pox as a child.

FAMILY HISTORY: 5 siblings (4 brothers), all healthy. Mother died of multiple myeloma (1990). Father, grandparents, alive and healthy.

SOCIAL HISTORY: Gay lifestyle. Grew up and attended college in Minnesota. Moved to California in 1978. Substance abuse, but denies intravenous drug use.

(2) Clinical Course (a) Connective tissue disease—Diagnosis of scleroderma manifested by Raynaud's in hands and feet, sclerodactyly, microstomia, restrictive lung disease (by pulmonary function tests) and esophageal/GI signs and symptoms (esoph. manometry, 1983). Also Sjogren's syndrome, with lymphadenopathy prior to 1981.

(i) Laboratory analysis of 1981 specimen ANA(+), course speckled (antinuclear antibody test positive by immunofluorescence with pattern consistent with anti-RNP antibodies). Anti-RNP(+), 1981, by DD (double diffusion) at a 1:10 dilution versus U1 snRNP substrate. Anti-Scl-70(−) by RIA, 1981.

(ii) Laboratory analysis of 1992 blood specimen ANA(+) by IF (immunofluorescence); western blot (+) for anti 70K reactivity.

(b) HIV disease—Diffuse lymphadenopathy consistent with ARC (AIDS-related complex) noted in 1986. HIV(+), 1987; confirmed 1988. No reported AIDS-related symptoms in past 6 years. He is on prophylactic 100 mg ZDV, TID and 100 mg Acyclovir, TID, 1.5 yrs. Related labs are as follows:

| 1987, 1988 | October, 1988 |
|---|---|
| HW-1 (+) | WBC 7.0 |
| | CD4 + T cells 545 (cells/mm³) CD4/ |
| | CD8 0.29 |
| 1987 | 1989 |
| WBC 6.1 | WBC 8.4 |
| CD4 + T cells 504 (cells/mm³) | CD4 + T cells 543 (cells/mm³) CD4/ |
| (25%, low nl) | CD8 0.3 |
| CD4/CD8 0.8 (low nl) | 1991 |
| total lymph count, 2015 (nl); total | WBC 7.3 |
| T, 62% (nl) | CD4 + T cells 565 (cells/mm³) CD4/ |
| HSV I IgG-neg | CD8 0.27 |
| HSV II IgG-neg | p24 core ag (−) |
| CMV IgG-neg | |
| April, 1988 | |
| WBC 6.8 | |
| CD4 + T cells 396 (cells/mm³) | |
| CD4/CD8 0.38 (low) | |

FIG. 10 shows a Western blot of Mr. M's 1981 and 1992 serum specimens relative to control HIV(+) and HIV(−) sera. Western blots shown in FIG. 10 were performed using an Organon Teknika kit. All sera were tested at dilutions of 1:50, as recommended by the supplier. Lanes 1–12, HIV(+) sera, included for reference. Lanes 13–15, high and low HIV sera and a negative control, from Organon Teknika, included for reference. Lanes 16 and 17, Mr. M.'s 1981 and 1992 specimens, respectively. Lanes 18–20, negative controls (laboratory personnel).

FIG. 10 shows the reactivity in an HIV western blot of Mr. M's 1981 and 1992 specimens (lanes 16 and 17). Despite high anti-RNP reactivity in 1981 (above), Mr. M proved HIV negative, further confirming that anti-RNP sera give a false positive by ELISA, not by Western blots. From Mr. M's 1992 specimen, it is apparent that he was definitely HIV-1 exposed.

(3) Analysis

Mr. M is definable as AIDS-free, on the basis of lacking an opportunistic infection, Kaposi's sarcoma or a lymphomatous disease. He has been seropositive for at least 7 years. His lack of prophylactic treatment for the first 3.5 years of his HIV(+) status is a relatively poor prognosticator for developing AIDS. However, in addition to lacking diagnostic criteria for AIDS, he reports feeling well, except for stiffness and pain related to his scleroderma. His laboratory tests are consistent with the following risk assessment:

(a) Risk for opportunistic infection: low, based on a CD4+T cell count of >500.

(b) An analysis of risk for progression to AIDS is based on a relative hazard index defined in relation to a gay, seronegative group. A relative hazard equal to this group has a value of 1. The most reliable prognosticating factor in this study was the CD4(+) T cell count. Mr. M.'s relative hazard based on this criteria is as follows:

| | |
|---|---|
| number of CD4 (+) T cells | 1.0 |
| % of total lymphocytes | 2.8 |
| number of CD8 (+) T cells | 1.1 |
| CD4/CD8 | 3.6 |
| p24 | 1.0 |

It should be noted that seronegative SRD patients also have anomalous T cell counts and CD4/CD8 ratios. Thus, in Mr. M's case, the relatively high risks related to % of lymphocytes and CD4/CD8 ratios may not be prognosticators of AIDS risk.

Based on this analysis, and on the negative screening tests for opportunistic pathogens and negative p24 antigen, Mr. M's case, after 5 years of seropositivity, is one of guarded optimism. The stability of his laboratory parameters over the last 7 years is encouraging, and particularly so because he was untreated for the first 3.5 years.

While there have been shown and described the fundamental novel features of the invention, it will be understood that various omissions, substitutions and changes in the form and details illustrated may be made by those skilled in the art without departing from the spirit of the invention. It is the intention to be limited only as indicated by the scope of the following claims.

TABLE I

SRDs and associated autoimmune conditions* producing autoantibodies to be used as therapies

| Primary SRD | Relevant Antibody Specificities | Composition of Relevant Antigen |
|---|---|---|
| Mixed connective tissue disease | anti-U1snRNP (anti-RNP) | U1RNA and associated polypeptide 70K |
| Scleroderma | anti-centromere | CENP-B |
| | Scl-70/topoisomerase | Single polypeptide |
| Systemic *lupus erythematosus* | anti-U1 snRNP | as above |
| Thyroid Disorders: | | |
| Hashimoto's thyroiditis; Graves disease | anti-thyroglobulin anti-TPO (microsomal) | thyroglobulin-h thyroid peroxidase (TPO) |

*Included in these are conditions in which individuals do not have manifestations of the SRDs but do, in fact, produce antibodies having any of the specificities described in this table.

TABLE II

Sequence homologies between viral proteins and the N and C termini of the 70-kDa protein.

| Sequence | Location in the 70-kDa protein | Number of amino acid | Virus (protein) | Number of amino acid |
|---|---|---|---|---|
| N terminus | | | | |
| SGGGGS SEQ ID NO: 76 | 5–10 | 6 | HSV-1 (IE) | 6 |
| SGGGG SEQ ID NO: 77 | 5–9 | 5 | HSV-1 (pol) | 5 |
| GERLD SEQ ID NO: 78 | 64–68 | 5 | HSV-1 (TK) | 5 |
| PAARP SEQ ID NO: 79 | 94–98 | 5 | HSV-1 (DNA binding) | 5 |
| AASSA SEQ ID NO: 80 | 101–105 | 5 | HSV-1 (IE) | 5 |
| VEAEAG SEQ ID NO: 81 | 143–148 | 6 | HSV-1 (IE) | 6 |
| AEAGVS SEQ ID NO: 82 | 145–149 | 5 | SRV-1 (p27) | 5 |
| APRDP SEQ ID NO: 83 | 190–194 | 5 | HSV-1 (DNA binding) | 5 |
| RRQQE SEQ ID NO: 84 | 253–257 | 5 | HSV-1 (TK) | 5 |
| GERLD SEQ ID NO: 85 | 64–68 | 5 | HSV-2 (TK) | 5 |
| GRAAS SEQ ID NO: 86 | 99–103 | 5 | HSV-2 (TK) | 5 |
| AEAGV SEQ ID NO: 87 | 145–149 | 5 | SRV-1 (p27) | 5 |
| VAEGL SEQ ID NO: 88 | 151–155 | 5 | EBV (coat) | 5 |
| PQPPRA SEQ ID NO: 89 | 156–161 | 6 | Rubella | 6 |
| HNQPY SEQ ID NO: 90 | 210–214 | 5 | SV40 (large T) | 5 |
| PSPLP SEQ ID NO: 91 | 401–405 | 5 | CMV (early) | 5 |
| C terminus | | | | |
| RDRDRDR SEQ ID NO: 1 | 407–413 | 7 | HIV-1 (gp41) | 5 |
| GGGDM SEQ ID NO: 98 | 488–492 | 5 | HIV-1 (gp120) | 5 |
| RDRDR SEQ ID NO: 60 | 524–528 | 5 | HIV-1 (gp41) | 5 |
| RDRDRDRDRDR SEQ ID NO: 93 | 542–552 | 11 | HIV-1 (gp41) | 5 |
| ERGRD SEQ ID NO: 94 | 562–566 | 5 | HIV-1 (gp41) | 5 |
| GLEGL SEQ ID NO: 95 | 578–582 | 5 | HIV-1 (3' orf) | 5 |
| RSSRS SEQ ID NO: 96 | 467–471 | 5 | SRV-1 (coat) | 5 |
| SRERAR SEQ ID NO: 97 | 471–476 | 6 | EBV (na) | 6 |
| DSRDM SEQ ID NO: 98 | 585–589 | 5 | EBV (93K) | 5 |
| DSRDM SEQ ID NO: 98 | 585–589 | 5 | EBV (140K reduc.) | 5 |
| GYLAP SEQ ID NO: 99 | 598–602 | 5 | HSV-1 (exo) | 5 |
| RERRE SEQ ID NO: 6 | 415–419 | 5 | p30 | 5 |

Sequences were retrieved from NBRF, GenBank, or EMBL banks, and homology comparisons were made. The N and C termini are defined as aa 1–106 and 407–631, respectively. The complete list of 20 viruses is reported in Table 1. gp. Glycoprotein: pol. polymerase; TK. thymidine kinase: SV40, simian virus 40: orf. open reading frame; reduc., reductase; exo, exonnuclease.
*Number of amino acids matching in the nuclear antigen and virus, respectively. All matches were verified against the published sequences.

TABLE III

Sequence homologies between viral proteins and the N and C termini of CENP-B.

| Protein Sequence | Location in CENP-B | Number of amino acid | Virus (protein) | Number of amino acid |
|---|---|---|---|---|
| N terminus | | | | |
| DQAAG SEQ ID NO: 100 | 201–205 | 5 | HSV-1 (DNA binding) | 5 |
| QAGLP SEQ ID NO: 101 | 249–253 | 5 | HSV-1 (gp-D) | 5 |
| LPVKG SEQ ID NO: 102 | 88–92 | 5 | SRV-1 (gag p27) | 5 |
| ETSLW SEQ ID NO: 103 | 191–195 | 5 | SRV-1 (protease) | 5 |
| ASQDV SEQ ID NO: 104 | 182–186 | 5 | HIV-1 (gag) | 5 |
| RTPAA SEQ ID NO: 105 | 144–148 | 5 | FeLV (12p) | 5 |
| LLLAG SEQ ID NO: 106 | 288–292 | 5 | FeLV (30p) | 5 |
| EGSGGS SEQ ID NO: 107 | 158–163 | 6 | EB-V (na) | 6 |
| LAGRL SEQ ID NO: 108 | 290–294 | 5 | EB-V (93k) | 5 |
| C terminus | | | | |
| EEEGE SEQ ID NO: 109 | 412–416 | 5 | HSV-1 (pol) | 5 |
| EEEGE SEQ ID NO: 109 | 421–425 | 5 | HSV-1 (pol) | 5 |
| QGVVE SEQ ID NO: 110 | 473–477 | 5 | HSV-1 (IE) | 5 |
| DEDDDD SEQ ID NO: 111 | 521–526 | 6 | HSV-1 (IE) | 6 |
| EDGDE SEQ ID NO: 112 | 528–532 | 5 | HSV-2 (pol) | 5 |
| EEEEE SEQ ID NO: 113 | 401–414 | 14 | MC29 (v-myc) | 5 |
| EEEEEE SEQ ID NO: 6 | 418–423 | 6 | MC29 (v-myc) | 5 |
| EEEEEE SEQ ID NO: 6 | 425–430 | 6 | MC29 (v-myc) | 5 |
| EEEEE SEQ ID NO: 113 | 453–457 | 5 | MC29 (v-myc) | 5 |
| EEDEE SEQ ID NO: 114 | 456–460 | 5 | MC29 (v-myc) | 5 |

TABLE III-continued

Sequence homologies between viral proteins and the N and C termini of CENP-B.

| Protein Sequence | Location in CENP-B | Number of amino acid | Virus (protein) | Number of amino acid |
|---|---|---|---|---|
| SDSEEE SEQ ID NO: 115 | 507–513 | 6 | MC29 (v-myc) | 6 |
| DSDEEE SEQ ID NO: 116 | 450–455 | 6 | CMV (gp-B) | 6 |
| DSDEE SEQ ID NO: 117 | 450–454 | 5 | CMV (LM-P) | 5 |
| DEDDDD SEQ ID NO: 118 | 521–526 | 6 | CMV (30K) | 6 |
| EEEGGE SEQ ID NO: 64 | 428–433 | 6 | HIV-1 (gp41) | 6 |
| EEEEV SEQ ID NO: 119 | 439–443 | 5 | HIV-1 (3' orf) | 5 |
| FAMVK SEQ ID NO: 120 | 546–550 | 5 | SRV-1 (pol) | 5 |
| DDDDE SEQ ID NO: 121 | 524–528 | 5 | SV40 (large T) | 5 |

Retrieval of viral sequences from protein and gene banks and matching to CENP-B was performed as described in Table 1. The N and C termini are defined as aa 1–400 and 401–594, respectively. Abbreviations are the same as in Table 2.

TABLE IV

Neutralization of HIV-1 strains III B and MN by select autoimmune antibody containing sera.

| Serum | | Strain IIIB Vn/Vo | | Strain MN Vn/Vo |
|---|---|---|---|---|
| 1. HIV-1 infected | 1:8 | 0.004 | 1. HIV infected | 0.002 |
| | 1:16 | 0.004 | | 0.002 |
| | 1:32 | 0.004 | | 0.002 |
| | 1:64 | 0.004 | | 0.002 |
| 2. Anti- | 1:8 | 0.40 | 2. Anti- | 1+ |
| centromere | 1:16 | 0.54 | centromere | 1+ |
| | 1:32 | 0.68 | | 1+ |
| | 1:64 | 0.77 | | 1+ |
| 3. Anti-RNP | 1:8 | 0.004 | 3. Anti-RNP | 0.002 |
| | 1:16 | 0.004 | | 0.002 |
| | 1:32 | 0.004 | | 0.002 |
| | 1:64 | 0.004 | | 0.002 |
| 4. Other | 1:8 | 0.03 | 4. Other | 1:8 | 0.04 |
| autoimmune | 1:16 | 0.08 | autoimmune | 1:16 | 0.06 |
| antibody | 1:32 | 0.14 | antibody | 1:32 | 0.07 |
| containing | 1:64 | 0.43 | containing | 1:64 | 0.22 |
| serum* | | | serum | | |

*Included in these are conditions in which individuals do not have manifestations of the SRDs but do, in fact, produce antibodies having any of the specificities described in this table.

SEQUENCE LISTING ( 1 ) GENERAL INFORMATION:

( i i i ) NUMBER OF SEQUENCES: 121

( 2 ) INFORMATION FOR SEQ ID NO:1:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( x i ) SEQUENCE DESCRIPTION: SEQ ID NO:1:

Arg Asp Arg Asp Arg Asp Arg
1               5

( 2 ) INFORMATION FOR SEQ ID NO:2:

(i) SEQUENCE CHARACTERISTICS:
   (A) LENGTH: 12 amino acids
   (B) TYPE: amino acid
   (D) TOPOLOGY: linear (ii) MOLECULE TYPE: peptide (xi) SEQUENCE DESCRIPTION: SEQ ID NO:2:

Arg Glu Arg Glu Arg Glu Arg Glu Arg Glu Arg Glu
1               5                   10

(2) INFORMATION FOR SEQ ID NO:3:

(i) SEQUENCE CHARACTERISTICS:
      (A) LENGTH: 8 amino acids
      (B) TYPE: amino acid
      (D) TOPOLOGY: linear (ii) MOLECULE TYPE: peptide (xi) SEQUENCE DESCRIPTION: SEQ ID NO:3:

Arg Arg Glu Glu Arg Arg Glu Glu
1               5

(2) INFORMATION FOR SEQ ID NO:4:

(i) SEQUENCE CHARACTERISTICS:
      (A) LENGTH: 6 amino acids
      (B) TYPE: amino acid
      (D) TOPOLOGY: linear (ii) MOLECULE TYPE: peptide (xi) SEQUENCE DESCRIPTION: SEQ ID NO:4:

Arg Arg Glu Arg Arg Glu
1               5

(2) INFORMATION FOR SEQ ID NO:5:

(i) SEQUENCE CHARACTERISTICS:
      (A) LENGTH: 7 amino acids
      (B) TYPE: amino acid
      (D) TOPOLOGY: linear (ii) MOLECULE TYPE: peptide (xi) SEQUENCE DESCRIPTION: SEQ ID NO:5:

Lys Glu Lys Glu Lys Glu Lys
1               5

(2) INFORMATION FOR SEQ ID NO:6:

(i) SEQUENCE CHARACTERISTICS:
      (A) LENGTH: 6 amino acids
      (B) TYPE: amino acid
      (D) TOPOLOGY: linear (ii) MOLECULE TYPE: peptide (xi) SEQUENCE DESCRIPTION: SEQ ID NO:6:

Glu Glu Glu Glu Glu Glu
1               5

(2) INFORMATION FOR SEQ ID NO:7:

(i) SEQUENCE CHARACTERISTICS:
      (A) LENGTH: 9 amino acids
      (B) TYPE: amino acid
      (D) TOPOLOGY: linear ( i i ) MOLECULE TYPE: peptide ( x i ) SEQUENCE DESCRIPTION: SEQ ID NO:7:

Glu Asp Asp Glu Glu Asp Glu Asp Glu
1               5

( 2 ) INFORMATION FOR SEQ ID NO:8:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:8:

Asp Asp Asp Asp Asp Asp
1               5

( 2 ) INFORMATION FOR SEQ ID NO:9:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:9:

Arg Arg Arg Arg Arg Arg
1               5

( 2 ) INFORMATION FOR SEQ ID NO:10:

( i ) SEQUENCE CHARACTERISTICS:
  ( A ) LENGTH: 7 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:10:

Arg Lys Arg Lys Arg Lys Lys
1               5

( 2 ) INFORMATION FOR SEQ ID NO:11:

( i ) SEQUENCE CHARACTERISTICS:
  ( A ) LENGTH: 7 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:11:

Lys Lys Lys Lys Lys Lys Lys
1               5

( 2 ) INFORMATION FOR SEQ ID NO:12:

( i ) SEQUENCE CHARACTERISTICS:
  ( A ) LENGTH: 7 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:12:

Glu Arg Asp Arg Asp Arg Asp

```
    1               5
```

(2) INFORMATION FOR SEQ ID NO:13:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:13:

```
    Arg  Glu  Arg  Arg  Arg
    1                    5
```

(2) INFORMATION FOR SEQ ID NO:14:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:14:

```
    Arg  Arg  Glu  Arg  Glu
    1                    5
```

(2) INFORMATION FOR SEQ ID NO:15:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:15:

```
    Glu  Arg  Glu  Glu  Glu  Arg
    1                    5
```

(2) INFORMATION FOR SEQ ID NO:16:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:16:

```
    Glu  Asp  Asp  Glu  Glu
    1                    5
```

(2) INFORMATION FOR SEQ ID NO:17:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:17:

```
    Asp  Asp  Asp  Glu  Glu  Asp
    1                    5
```

(2) INFORMATION FOR SEQ ID NO:18:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:18:

Asp Glu Glu Glu Asp Asp Glu
1               5

( 2 ) INFORMATION FOR SEQ ID NO:19:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

Glu Asp Glu Asp Asp Asp
1               5

( 2 ) INFORMATION FOR SEQ ID NO:20:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

Ser Ser Ser Gly Arg
1               5

( 2 ) INFORMATION FOR SEQ ID NO:21:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

Arg Leu Gly Gly Gly Leu Arg Arg Thr Arg Asp Gly Gly
1               5                   10

( 2 ) INFORMATION FOR SEQ ID NO:22:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

Glu Leu Leu Gly Arg Arg Gly Trp Glu Ala
1               5                   10

( 2 ) INFORMATION FOR SEQ ID NO:23:

( i ) SEQUENCE CHARACTERISTICS:
        ( A ) LENGTH: 24 amino acids
        ( B ) TYPE: amino acid
        ( D ) TOPOLOGY: linear (i i) MOLECULE TYPE: peptide (x i) SEQUENCE DESCRIPTION: SEQ ID NO:23:

```
Gly Glu Arg Leu Asp Arg Arg Lys Glu Arg Arg Arg Gln Glu Ala Leu
1               5                   10                  15

Ile Glu Asp Gln Gln Gln Arg Gln
              20
```

(2) INFORMATION FOR SEQ ID NO:24:

(i) SEQUENCE CHARACTERISTICS:
        (A) LENGTH: 17 amino acids
        (B) TYPE: amino acid
        (D) TOPOLOGY: linear (i i) MOLECULE TYPE: peptide (x i) SEQUENCE DESCRIPTION: SEQ ID NO:24:

```
Pro Gly Arg Ala Ala Ser Ser Ala Gly Ile Gly Gly Arg Gln Gly Leu
1               5                   10                  15

Leu
```

(2) INFORMATION FOR SEQ ID NO:25:

(i) SEQUENCE CHARACTERISTICS:
        (A) LENGTH: 10 amino acids
        (B) TYPE: amino acid
        (D) TOPOLOGY: linear (i i) MOLECULE TYPE: peptide (x i) SEQUENCE DESCRIPTION: SEQ ID NO:25:

```
Ser Gly Leu Val Arg Ser Ser Ser Gly Arg
1               5                   10
```

(2) INFORMATION FOR SEQ ID NO:26:

(i) SEQUENCE CHARACTERISTICS:
        (A) LENGTH: 10 amino acids
        (B) TYPE: amino acid
        (D) TOPOLOGY: linear (i i) MOLECULE TYPE: peptide (x i) SEQUENCE DESCRIPTION: SEQ ID NO:26:

```
Pro Arg Ala Ser Gly Gln Thr Pro Glu Arg
1               5                   10
```

(2) INFORMATION FOR SEQ ID NO:27:

(i) SEQUENCE CHARACTERISTICS:
        (A) LENGTH: 10 amino acids
        (B) TYPE: amino acid
        (D) TOPOLOGY: linear (i i) MOLECULE TYPE: peptide (x i) SEQUENCE DESCRIPTION: SEQ ID NO:27:

```
Thr Arg Glu Glu Arg Met Glu Arg Lys Arg
1               5                   10
```

(2) INFORMATION FOR SEQ ID NO:28:

(i) SEQUENCE CHARACTERISTICS:
        (A) LENGTH: 21 amino acids
        (B) TYPE: amino acid
        (D) TOPOLOGY: linear (i i) MOLECULE TYPE: peptide (x i) SEQUENCE DESCRIPTION: SEQ ID NO:28:

Ser Lys Leu Arg Arg Glu Phe Glu Val Tyr Gly Pro Ile Lys Arg Ile
1               5                   10                  15

His Met Val Tyr Ser
            20

(2) INFORMATION FOR SEQ ID NO:29:

(i) SEQUENCE CHARACTERISTICS:
        (A) LENGTH: 9 amino acids
        (B) TYPE: amino acid
        (D) TOPOLOGY: linear (i i) MOLECULE TYPE: peptide (x i) SEQUENCE DESCRIPTION: SEQ ID NO:29:

Gly Tyr Ala Phe Ile Glu Tyr Glu His
1               5

(2) INFORMATION FOR SEQ ID NO:30:

(i) SEQUENCE CHARACTERISTICS:
        (A) LENGTH: 22 amino acids
        (B) TYPE: amino acid
        (D) TOPOLOGY: linear (i i) MOLECULE TYPE: peptide (x i) SEQUENCE DESCRIPTION: SEQ ID NO:30:

Pro Arg Arg Leu Gly Gly Gly Leu Gly Gly Thr Arg Arg Gly Gly Ala
1               5                   10                  15

Asp Val Asn Ile Arg His
            20

(2) INFORMATION FOR SEQ ID NO:31:

(i) SEQUENCE CHARACTERISTICS:
        (A) LENGTH: 7 amino acids
        (B) TYPE: amino acid
        (D) TOPOLOGY: linear (i i) MOLECULE TYPE: peptide (x i) SEQUENCE DESCRIPTION: SEQ ID NO:31:

Arg Asp Arg Asp Arg Asp Arg
1               5

(2) INFORMATION FOR SEQ ID NO:32:

(i) SEQUENCE CHARACTERISTICS:
        (A) LENGTH: 10 amino acids
        (B) TYPE: amino acid
        (D) TOPOLOGY: linear (i i) MOLECULE TYPE: peptide (x i) SEQUENCE DESCRIPTION: SEQ ID NO:32:

Glu Leu Arg Gly Gly Gly Gly Asp Met Ala
1               5                   10

(2) INFORMATION FOR SEQ ID NO:33:

(i) SEQUENCE CHARACTERISTICS:
        (A) LENGTH: 18 amino acids
        (B) TYPE: amino acid
        (D) TOPOLOGY: linear ( i i ) MOLECULE TYPE: peptide ( x i ) SEQUENCE DESCRIPTION: SEQ ID NO:33:

```
Gly  Pro  Asp  Gly  Pro  Asp  Gly  Pro  Glu  Glu  Lys  Gly  Arg  Asp  Arg  Asp
1                   5                        10                       15

Arg  Glu
```

( 2 ) INFORMATION FOR SEQ ID NO:34:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:34:

```
Arg  Asp  Arg  Asp  Arg  Asp  Arg  Asp  Arg  Asp  Arg
1                   5                        10
```

( 2 ) INFORMATION FOR SEQ ID NO:35:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:35:

```
Gly  Gly  Gly  Gly  Gly  Gln  Asp  Asn
1                   5
```

( 2 ) INFORMATION FOR SEQ ID NO:36:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:36:

```
Gly  Ile  Glu  Glu  Glu  Gly  Glu  Arg  Asp  Arg  Asp  Arg  Ser  Ile  Arg
1                   5                        10                       15
```

( 2 ) INFORMATION FOR SEQ ID NO:37:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:37:

```
Leu  Ile  Glu  Glu  Ser  Gln  Asn  Gln  Gln
1                   5
```

( 2 ) INFORMATION FOR SEQ ID NO:38:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:38:

Pro Gly Arg Ala Phe Val Thr Ile Gly
1               5

( 2 ) INFORMATION FOR SEQ ID NO:39:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:39:

Gln Leu Leu Gly
1

( 2 ) INFORMATION FOR SEQ ID NO:40:

( i ) SEQUENCE CHARACTERISTICS:
( A ) LENGTH: 8 amino acids
( B ) TYPE: amino acid
( D ) TOPOLOGY: linear ( i i ) MOLECULE TYPE: peptide ( x i ) SEQUENCE DESCRIPTION: SEQ ID NO:40:

Ser Gly Gln Ile Arg Cys Ser Ser
1               5

( 2 ) INFORMATION FOR SEQ ID NO:41:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( x i ) SEQUENCE DESCRIPTION: SEQ ID NO:41:

Pro Arg Arg Ile Arg Gln Gly Leu Glu Arg
1               5                   10

( 2 ) INFORMATION FOR SEQ ID NO:42:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( x i ) SEQUENCE DESCRIPTION: SEQ ID NO:42:

Thr Arg Pro Asn Asn Asn Thr Arg Lys Arg
1               5                   10

( 2 ) INFORMATION FOR SEQ ID NO:43:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( x i ) SEQUENCE DESCRIPTION: SEQ ID NO:43:

Ser Lys Leu Arg Glu Gln Phe
1               5

( 2 ) INFORMATION FOR SEQ ID NO:44:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:44:

Gly  Arg  Ala  Phe  Val  Thr  Ile  Gly  Lys
  1                      5

( 2 ) INFORMATION FOR SEQ ID NO:45:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:45:

Pro  Arg  Arg  Ile  Arg  Gln  Gly  Leu
  1                      5

( 2 ) INFORMATION FOR SEQ ID NO:46:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:46:

Gly  Ala  Cys  Arg  Ala  Ile  Arg  His
  1                      5

( 2 ) INFORMATION FOR SEQ ID NO:47:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:47:

Glu  Arg  Asp  Arg  Asp  Arg
  1                      5

( 2 ) INFORMATION FOR SEQ ID NO:48:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:48:

Glu  Phe  Leu  Arg  Gly  Gly  Gly  Asp  Met
  1                      5

( 2 ) INFORMATION FOR SEQ ID NO:49:

( i ) SEQUENCE CHARACTERISTICS:
        ( A ) LENGTH: 19 amino acids (B) TYPE: amino acid
            (D) TOPOLOGY: linear (ii) MOLECULE TYPE: peptide (xi) SEQUENCE DESCRIPTION: SEQ ID NO:49:

Gly Pro Asp Arg Pro Glu Gly Ile Glu Glu Gly Gly Glu Arg Asp
    1               5                   10                  15

Arg Asp Arg (2) INFORMATION FOR SEQ ID NO:50:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (xi) SEQUENCE DESCRIPTION: SEQ ID NO:50:

Glu Arg Asp Arg Asp
    1               5

(2) INFORMATION FOR SEQ ID NO:51:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (xi) SEQUENCE DESCRIPTION: SEQ ID NO:51:

Gly Arg Ala Phe Val Thr Ile Gly
    1               5

(2) INFORMATION FOR SEQ ID NO:52:

(i) SEQUENCE CHARACTERISTICS:
            (A) LENGTH: 12 amino acids
            (B) TYPE: amino acid
            (D) TOPOLOGY: linear (ii) MOLECULE TYPE: peptide (xi) SEQUENCE DESCRIPTION: SEQ ID NO:52:

Arg Gly Pro Gly Arg Ala Phe Val Thr Ile Gly Lys
    1               5                   10

(2) INFORMATION FOR SEQ ID NO:53:

(i) SEQUENCE CHARACTERISTICS:
            (A) LENGTH: 12 amino acids
            (B) TYPE: amino acid
            (D) TOPOLOGY: linear (ii) MOLECULE TYPE: peptide (xi) SEQUENCE DESCRIPTION: SEQ ID NO:53:

Lys Lys Arg Gly Phe Gln Phe Val Thr Phe Asp Asp
    1               5                   10

(2) INFORMATION FOR SEQ ID NO:54:

(i) SEQUENCE CHARACTERISTICS:
            (A) LENGTH: 12 amino acids
            (B) TYPE: amino acid
            (D) TOPOLOGY: linear ( i i ) MOLECULE TYPE: peptide ( x i ) SEQUENCE DESCRIPTION: SEQ ID NO:54:

Lys Lys Arg Gly Phe Ala Phe Val Thr Phe Asp Asp
1               5                   10

( 2 ) INFORMATION FOR SEQ ID NO:55:

( i ) SEQUENCE CHARACTERISTICS:
       ( A ) LENGTH: 12 amino acids
       ( B ) TYPE: amino acid
       ( D ) TOPOLOGY: linear ( i i ) MOLECULE TYPE: peptide ( x i ) SEQUENCE DESCRIPTION: SEQ ID NO:55:

Lys Pro Arg Gly Tyr Ala Phe Ile Glu Tyr Glu His
1               5                   10

( 2 ) INFORMATION FOR SEQ ID NO:56:

( i ) SEQUENCE CHARACTERISTICS:
       ( A ) LENGTH: 12 amino acids
       ( B ) TYPE: amino acid
       ( D ) TOPOLOGY: linear ( i i ) MOLECULE TYPE: peptide ( x i ) SEQUENCE DESCRIPTION: SEQ ID NO:56:

Lys Ala Arg Gly Gln Ala Phe Val Ile Phe Lys Glu
1               5                   10

( 2 ) INFORMATION FOR SEQ ID NO:57:

( i ) SEQUENCE CHARACTERISTICS:
       ( A ) LENGTH: 12 amino acids
       ( B ) TYPE: amino acid
       ( D ) TOPOLOGY: linear ( i i ) MOLECULE TYPE: peptide ( x i ) SEQUENCE DESCRIPTION: SEQ ID NO:57:

Lys Met Arg Gly Gln Ala Phe Val Ile Phe Lys Glu
1               5                   10

( 2 ) INFORMATION FOR SEQ ID NO:58:

( i ) SEQUENCE CHARACTERISTICS:
       ( A ) LENGTH: 12 amino acids
       ( B ) TYPE: amino acid
       ( D ) TOPOLOGY: linear ( i i ) MOLECULE TYPE: peptide ( x i ) SEQUENCE DESCRIPTION: SEQ ID NO:58:

Arg Pro Arg Gly Val Ala Phe Val Arg Tyr Asn Lys
1               5                   10

( 2 ) INFORMATION FOR SEQ ID NO:59:

( i ) SEQUENCE CHARACTERISTICS:
       ( A ) LENGTH: 5 amino acids
       ( B ) TYPE: amino acid
       ( D ) TOPOLOGY: linear ( i i ) MOLECULE TYPE: peptide ( x i ) SEQUENCE DESCRIPTION: SEQ ID NO:59:

Arg Asp Arg Asp Arg (2) INFORMATION FOR SEQ ID NO:60:

(i) SEQUENCE CHARACTERISTICS:
    (A) LENGTH: 5 amino acids
    (B) TYPE: amino acid
    (D) TOPOLOGY: linear (ii) MOLECULE TYPE: peptide (xi) SEQUENCE DESCRIPTION: SEQ ID NO:60:

Arg  Glu  Arg  Arg  Glu
  1                   5

(2) INFORMATION FOR SEQ ID NO:61:

(i) SEQUENCE CHARACTERISTICS:
    (A) LENGTH: 4 amino acids
    (B) TYPE: amino acid
    (D) TOPOLOGY: linear (ii) MOLECULE TYPE: peptide (xi) SEQUENCE DESCRIPTION: SEQ ID NO:61:

Glu  Arg  Lys  Arg
  1

(2) INFORMATION FOR SEQ ID NO:62:

(i) SEQUENCE CHARACTERISTICS:
    (A) LENGTH: 11 amino acids
    (B) TYPE: amino acid
    (D) TOPOLOGY: linear (ii) MOLECULE TYPE: peptide (xi) SEQUENCE DESCRIPTION: SEQ ID NO:62:

Glu  Thr  Pro  Glu  Glu  Arg  Glu  Glu  Arg  Arg  Arg
  1                   5                        10

(2) INFORMATION FOR SEQ ID NO:63:

(i) SEQUENCE CHARACTERISTICS:
    (A) LENGTH: 6 amino acids
    (B) TYPE: amino acid
    (D) TOPOLOGY: linear (ii) MOLECULE TYPE: peptide (xi) SEQUENCE DESCRIPTION: SEQ ID NO:63:

Glu  Glu  Glu  Gly  Gly  Glu
  1                   5

(2) INFORMATION FOR SEQ ID NO:64:

(i) SEQUENCE CHARACTERISTICS:
    (A) LENGTH: 5 amino acids
    (B) TYPE: amino acid
    (D) TOPOLOGY: linear (ii) MOLECULE TYPE: peptide (xi) SEQUENCE DESCRIPTION: SEQ ID NO:64:

Glu  Glu  Glu  Gly  Glu
  1                   5

(2) INFORMATION FOR SEQ ID NO:65:

( i ) SEQUENCE CHARACTERISTICS:
  ( A ) LENGTH: 36 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:65:

```
Cys Thr Arg Pro Asn Asn Asn Thr Arg Lys Arg Ile Arg Ile Gln Arg
1               5                   10                  15
Gly Pro Gly Arg Ala Phe Val Thr Ile Gly Lys Ile Gly Asn Met Arg
            20                  25                  30
Gln Ala His Cys
            35
```

( 2 ) INFORMATION FOR SEQ ID NO:66:

( i ) SEQUENCE CHARACTERISTICS:
  ( A ) LENGTH: 10 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:66:

```
Thr Arg Glu Glu Arg Met Glu Arg Lys Arg
1               5                   10
```

( 2 ) INFORMATION FOR SEQ ID NO:67:

( i ) SEQUENCE CHARACTERISTICS:
  ( A ) LENGTH: 8 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:67:

```
Arg Gly Phe Ala Phe Val Thr Phe
1               5
```

( 2 ) INFORMATION FOR SEQ ID NO:68:

( i ) SEQUENCE CHARACTERISTICS:
  ( A ) LENGTH: 8 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:68:

```
Arg Gly Gln Ala Phe Val Ile Phe
1               5
```

( 2 ) INFORMATION FOR SEQ ID NO:69:

( i ) SEQUENCE CHARACTERISTICS:
  ( A ) LENGTH: 8 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:69:

```
Arg Gly Tyr Ala Phe Ile Glu Tyr
1               5
```

( 2 ) INFORMATION FOR SEQ ID NO:70:

( i ) SEQUENCE CHARACTERISTICS:
  ( A ) LENGTH: 15 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:70:

```
Arg Lys Ser Ile Arg Ile Gln Arg Gly Pro Gly Arg Ala Phe Val
1               5                   10                  15
```

( 2 ) INFORMATION FOR SEQ ID NO:71:

( i ) SEQUENCE CHARACTERISTICS:
  ( A ) LENGTH: 10 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:71:

```
Gly Pro Gly Arg Ala Phe Val Thr Ile Gly
1               5                   10
```

( 2 ) INFORMATION FOR SEQ ID NO:72:

( i ) SEQUENCE CHARACTERISTICS:
  ( A ) LENGTH: 15 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:72:

```
Ile Arg Ile Gln Arg Gly Pro Gly Arg Ala Phe Val Thr Ile Gly
1               5                   10                  15
```

( 2 ) INFORMATION FOR SEQ ID NO:73:

( i ) SEQUENCE CHARACTERISTICS:
  ( A ) LENGTH: 11 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:73:

```
Arg Gly Pro Gly Arg Ala Phe Val Thr Ile Gly
1               5                   10
```

( 2 ) INFORMATION FOR SEQ ID NO:74:

( i ) SEQUENCE CHARACTERISTICS:
  ( A ) LENGTH: 11 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:74:

```
Arg Gly Pro Gly Arg Ala Phe Val Thr Ile Gly
1               5                   10
```

( 2 ) INFORMATION FOR SEQ ID NO:75:

( i ) SEQUENCE CHARACTERISTICS:
  ( A ) LENGTH: 164 base pairs
  ( B ) TYPE: nucleic acid
  ( C ) STRANDEDNESS: single ( D ) TOPOLOGY: linear ( i i ) MOLECULE TYPE: RNA (genomic)

( x i ) SEQUENCE DESCRIPTION: SEQ ID NO:75:

| AUACUUACCU | GGCAGGGGAG | AUACCAUGAU | CAUGAAGGUG | GUUCUCCCAG | GGCGAGGCUC | 60 |
| AGCCAUUGCA | CUCCGGUUGU | GCUGACCCCU | GCGAUUUCCC | CAAAUGCGGG | AAACUCGACU | 120 |
| GCAUAAUUUC | UGGUAGUGGG | GGACUGCGUU | CGCGCUUUCC | CCUG | | 164 |

( 2 ) INFORMATION FOR SEQ ID NO:76:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:76:

Ser Gly Gly Gly Gly Ser
1               5

( 2 ) INFORMATION FOR SEQ ID NO:77:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:77:

Ser Gly Gly Gly Gly
1               5

( 2 ) INFORMATION FOR SEQ ID NO:78:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:78:

Gly Glu Arg Leu Asp
1               5

( 2 ) INFORMATION FOR SEQ ID NO:79:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:79:

Pro Ala Ala Arg Pro
1               5

( 2 ) INFORMATION FOR SEQ ID NO:80:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:80:

Ala Ala Ser Ser Ala
1               5

( 2 ) INFORMATION FOR SEQ ID NO:81:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:81:

Val Glu Ala Glu Ala Gly
1               5

( 2 ) INFORMATION FOR SEQ ID NO:82:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:82:

Ala Glu Ala Gly Val Ser
1               5

( 2 ) INFORMATION FOR SEQ ID NO:83:

( i ) SEQUENCE CHARACTERISTICS:
  ( A ) LENGTH: 5 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:83:

Ala Pro Arg Asp Pro
1               5

( 2 ) INFORMATION FOR SEQ ID NO:84:

( i ) SEQUENCE CHARACTERISTICS:
  ( A ) LENGTH: 5 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:84:

Arg Arg Gln Gln Glu
1               5

( 2 ) INFORMATION FOR SEQ ID NO:85:

( i ) SEQUENCE CHARACTERISTICS:
  ( A ) LENGTH: 5 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:85:

Gly Glu Arg Leu Asp (2) INFORMATION FOR SEQ ID NO:86:

(i) SEQUENCE CHARACTERISTICS:
       (A) LENGTH: 5 amino acids
       (B) TYPE: amino acid
       (D) TOPOLOGY: linear (ii) MOLECULE TYPE: peptide (xi) SEQUENCE DESCRIPTION: SEQ ID NO:86:

Gly Arg Ala Ala Ser
   1               5

(2) INFORMATION FOR SEQ ID NO:87:

(i) SEQUENCE CHARACTERISTICS:
       (A) LENGTH: 5 amino acids
       (B) TYPE: amino acid
       (D) TOPOLOGY: linear (ii) MOLECULE TYPE: peptide (xi) SEQUENCE DESCRIPTION: SEQ ID NO:87:

Ala Glu Ala Gly Val
   1               5

(2) INFORMATION FOR SEQ ID NO:88:

(i) SEQUENCE CHARACTERISTICS:
       (A) LENGTH: 5 amino acids
       (B) TYPE: amino acid
       (D) TOPOLOGY: linear (ii) MOLECULE TYPE: peptide (xi) SEQUENCE DESCRIPTION: SEQ ID NO:88:

Val Ala Glu Gly Leu
   1               5

(2) INFORMATION FOR SEQ ID NO:89:

(i) SEQUENCE CHARACTERISTICS:
       (A) LENGTH: 6 amino acids
       (B) TYPE: amino acid
       (D) TOPOLOGY: linear (ii) MOLECULE TYPE: peptide (xi) SEQUENCE DESCRIPTION: SEQ ID NO:89:

Pro Gln Pro Pro Arg Ala
   1               5

(2) INFORMATION FOR SEQ ID NO:90:

(i) SEQUENCE CHARACTERISTICS:
       (A) LENGTH: 5 amino acids
       (B) TYPE: amino acid
       (D) TOPOLOGY: linear (ii) MOLECULE TYPE: peptide (xi) SEQUENCE DESCRIPTION: SEQ ID NO:90:

His Asn Gln Pro Tyr
   1               5

(2) INFORMATION FOR SEQ ID NO:91:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:91:

```
Pro  Ser  Pro  Leu  Pro
1                   5
```

( 2 ) INFORMATION FOR SEQ ID NO:92:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:92:

```
Gly  Gly  Gly  Asp  Met
1                   5
```

( 2 ) INFORMATION FOR SEQ ID NO:93:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:93:

```
Arg  Asp  Arg  Asp  Arg  Asp  Arg  Asp  Arg  Asp  Arg
1                   5                        10
```

( 2 ) INFORMATION FOR SEQ ID NO:94:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:94:

```
Glu  Arg  Gly  Arg  Asp
1                   5
```

( 2 ) INFORMATION FOR SEQ ID NO:95:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:95:

```
Gly  Leu  Glu  Gly  Leu
1                   5
```

( 2 ) INFORMATION FOR SEQ ID NO:96:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:96:

Arg Ser Ser Arg Ser
1               5

( 2 ) INFORMATION FOR SEQ ID NO:97:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:97:

Ser Arg Glu Arg Ala Arg
1               5

( 2 ) INFORMATION FOR SEQ ID NO:98:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:98:

Asp Ser Arg Asp Met
1               5

( 2 ) INFORMATION FOR SEQ ID NO:99:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:99:

Gly Tyr Leu Ala Pro
1               5

( 2 ) INFORMATION FOR SEQ ID NO:100:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:100:

Asp Gln Ala Ala Gly
1               5

( 2 ) INFORMATION FOR SEQ ID NO:101:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:101:

Gln Ala Gly Leu Pro ( 2 ) INFORMATION FOR SEQ ID NO:102:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:102:

```
Leu  Pro  Val  Lys  Gly
1                    5
```

( 2 ) INFORMATION FOR SEQ ID NO:103:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:103:

```
Glu  Thr  Ser  Leu  Trp
1                    5
```

( 2 ) INFORMATION FOR SEQ ID NO:104:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:104:

```
Ala  Ser  Gln  Asp  Val
1                    5
```

( 2 ) INFORMATION FOR SEQ ID NO:105:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:105:

```
Arg  Thr  Pro  Ala  Ala
1                    5
```

( 2 ) INFORMATION FOR SEQ ID NO:106:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:106:

```
Leu  Leu  Leu  Ala  Gly
1                    5
```

( 2 ) INFORMATION FOR SEQ ID NO:107:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:107:

Glu Gly Ser Gly Gly Ser
1               5

( 2 ) INFORMATION FOR SEQ ID NO:108:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:108:

Leu Ala Gly Arg Leu
1               5

( 2 ) INFORMATION FOR SEQ ID NO:109:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:109:

Glu Glu Glu Gly Glu
1               5

( 2 ) INFORMATION FOR SEQ ID NO:110:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:110:

Gln Gly Val Val Glu
1               5

( 2 ) INFORMATION FOR SEQ ID NO:111:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:111:

Asp Glu Asp Asp Asp Asp
1               5

( 2 ) INFORMATION FOR SEQ ID NO:112:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:112:

Glu Asp Gly Asp Glu
1               5

( 2 ) INFORMATION FOR SEQ ID NO:113:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:113:

Glu Glu Glu Glu Glu
1               5

( 2 ) INFORMATION FOR SEQ ID NO:114:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:114:

Glu Glu Asp Glu Glu
1               5

( 2 ) INFORMATION FOR SEQ ID NO:115:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:115:

Ser Asp Ser Glu Glu Glu
1               5

( 2 ) INFORMATION FOR SEQ ID NO:116:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:116:

Asp Ser Asp Glu Glu Glu
1               5

( 2 ) INFORMATION FOR SEQ ID NO:117:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:117:

Asp Ser Asp Glu Glu (2) INFORMATION FOR SEQ ID NO:118:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:118:

Asp  Glu  Asp  Asp  Asp  Asp
    1                          5

(2) INFORMATION FOR SEQ ID NO:119:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:119:

Glu  Glu  Glu  Glu  Val
    1                      5

(2) INFORMATION FOR SEQ ID NO:120:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:120:

Phe  Ala  Met  Val  Lys
    1                      5

(2) INFORMATION FOR SEQ ID NO:121:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:121:

Asp  Asp  Asp  Asp  Glu
    1                      5

We claim:

1. A method of treating an individual infected with the human immunodeficiency virus type 1 (HIV-1), said method comprising administering to said HIV-1-infected individual a therapeutically effective amount of a pharmaceutical composition comprising antibodies specific for the U1 small nuclear ribonuclear protein (U1-snRNP), said U1-snRNP-specific antibodies being capable of crossreacting with HIV-1 gp120 or gp41 envelope proteins in a manner sufficient to neutralize the HIV-1 virus.

* * * * *

UNITED STATES PATENT AND TRADEMARK OFFICE
CERTIFICATE OF CORRECTION

PATENT NO. : 5,707,626
DATED : January 13, 1998
INVENTOR(S) : Angeline S. Douvas et al.

It is certified that error appears in the above-identified patent and that said Letters Patent is hereby corrected as shown below:

The following cited references should be included in the list at page 4:

CELL, Vol. 51, No. 2, 23 Oct. 1987, Cambridge, NA US, pgs. 211-1\220 C.C.Query & J.D.Keene "A human autoimmune protein associated with U1 RNA contains a region of homology that is cross-reactive with retroviral p30gag antigen"

THE JOURNAL OF EXPERIMENTAL MEDICINE, Vol. 171 No. 3, 1 March 1990, pgs 819-829, Guldner, et al., "Human anti-P68 autoantibodies recognize a common epitope of U1 RNA containing small nuclear ribonucleoprotein and Influenza B virus"

AIDS RESEARCH AND HUMAN RETROVIRUS, Vol. 10 No. 3, March 1994, New York, USA, pgs 253-262 Douvas, et al., 'Cross-reactivity between autoimmune anti-U1 snRNP antibodies and neutralizing epitopes of HIV-1 gp120/141.

Signed and Sealed this

Fifth Day of May, 1998

*Attest:*

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO.    : 5,707,626
DATED         : January 13, 1998
INVENTOR(S)   : Douvas et al.

It is certified that error appears in the above-identified patent and that said Letters Patent is hereby corrected as shown below:

Title page, Item [54] and Column 1, line 2,
Title, "U2" should read -- U1 --

Title page,
Item [57], ABSTRACT,
Line 7, before "U1" insert -- of --

Column 1,
Line 54, "Leukaemia" change to -- Leukemia --
Line 66, "in vitro" should be -- *in vitro* --

Column 2,
Line 1, "Sjogren" change to -- Sjögren --
Line 15, "Klebsiella" change to -- *Klebsiella* --
Line 17, "Catin" change to -- Cain --
Lines 37 and 46, "70-Kda" change to -- 70-kDa --
Line 52, "68-kda" change to -- 70-kDa --

Column 3,
Line 27, "$\geqq$" change to -- $\geq$ --
Line 65, "in vitro" change to -- *in vitro* --

Column 4,
Line 3, after "(1985)" and before the period insert -- ] --

Column 6,
Line 12, "J. Cell. Biol." change to -- *J. Cell Biol.* -- and ":" change to -- , --
Line 36, after "]" insert -- . --
Line 54, "CDNA" change to -- cDNA --

Column 7,
Line 45, after "*Biochem*" insert -- . --

Column 8,
Line 18, after "*J*" insert -- . --
Line 19, delete "delete "]"
Line 51, "$\geqq$" change to -- $\geq$ --
Line 64, "141." change to -- 141, --
Line 64, delete "Vol."

UNITED STATES PATENT AND TRADEMARK OFFICE
CERTIFICATE OF CORRECTION

PATENT NO. : 5,707,626
DATED : January 13, 1998
INVENTOR(S) : Douvas et al.

It is certified that error appears in the above-identified patent and that said Letters Patent is hereby corrected as shown below:

Column 9,
Line 16, after "*Chem*", insert -- . --
Line 21, "SN RNAs", should read -- snRNAs --
Line 22, "In Situ", should read -- *In Situ* --
Lines 27 and 33, "NO:60" should read -- NO:52 --
Line 45, after "NO:61" insert -- , --

Column 10,
Line 7, delete second occurrence of "*Res.*"
Line 39, after "]" insert -- . --
Line 47, "overly" should read -- overlie --
Line 53, "70" should read -- 70k --
Line 63, "western" should read -- Western --

Column 11,
Line 3, "seropositivity" should read -- sero-positivity --
Line 42, "horse radish" should read -- horse-radish --
Line 63, gp-120" should read -- gp 120 -- and "pg41" should read -- gp41 --

Column 12,
Lines 1 and 6, "western" should read -- Western --
Line 17, "western" should read -- Western -- and "horse radish" should read -- horse-radish --
Line 28, "lane 7" should be -- Lane 7 --
Line 29, "lanes 12-14" should be -- Lanes 12-14 --

Column 13,
Line 42, "c-fos" should be -- *c-fos* --
Line 53, "Methylpiperazone" should read -- methylpiperazine --
Line 60, "in vitro" should be -- *in vitro* --

Column 14,
Line 33, ";" should be -- . --
Line 34, "$V_3$" should read -- V3 --
Lines 41 and 47, "in vitro" should be -- *in vitro* --

Column 15,
Line 27, "complication" should read -- complications --
Line 43, "," should be -- . --

UNITED STATES PATENT AND TRADEMARK OFFICE
CERTIFICATE OF CORRECTION

PATENT NO. : 5,707,626
DATED : January 13, 1998
INVENTOR(S) : Douvas et al.

It is certified that error appears in the above-identified patent and that said Letters Patent is hereby corrected as shown below:

Column 16,
Line 17, "complementarity" should be -- complementary --

Column 19,
Line 60, "Shamrock" should be -- Sambrook --
Line 61, "Shambrook" should be -- Sambrook --
Line 62, after "1989" add -- ) --

Column 21,
Line 15, "western blot" should be -- Western Blot --
Line 23, "HW" should be -- HIV --

Column 23,
Table II, "98" should be -- 92 --
Table II, "6" should be -- 61 --

Column 25,
Table IV, between the first and second "Vn/Vo" insert -- Serum --

Column 26,
Table IV, between the first and second "Vn/Vo" insert -- Serum --

Signed and Sealed this

Fifth Day of April, 2005

JON W. DUDAS
*Director of the United States Patent and Trademark Office*